US012765583B2

(12) United States Patent
Akimitsu et al.

(10) Patent No.: US 12,765,583 B2
(45) Date of Patent: Oct. 20, 2026

(54) METHOD FOR MASS-PRODUCING SWEETENER HAVING TASTE QUALITY SIMILAR TO THAT OF SUGAR AND HAVING D-ALLULOSE FUNCTIONALITY

(71) Applicant: NATIONAL UNIVERSITY CORPORATION KAGAWA UNIVERSITY, Takamatsu (JP)

(72) Inventors: Kazuya Akimitsu, Takamatsu (JP); Ken Izumori, Takamatsu (JP); Akihide Yoshihara, Takamatsu (JP); Seizo Takaoka, Takamatsu (JP); Shiro Kato, Takamatsu (JP); Susumu Mochizuki, Takamatsu (JP)

(73) Assignee: NATIONAL UNIVERSITY CORPORATION KAGAWA UNIVERSITY, Takamatsu (JP)

( * ) Notice: Subject to any disclaimer, the term of this patent is extended or adjusted under 35 U.S.C. 154(b) by 378 days.

(21) Appl. No.: 18/558,624

(22) PCT Filed: May 7, 2021

(86) PCT No.: PCT/JP2021/017565
§ 371 (c)(1),
(2) Date: Nov. 2, 2023

(87) PCT Pub. No.: WO2022/234671
PCT Pub. Date: Nov. 10, 2022

(65) Prior Publication Data

US 2024/0225064 A1 Jul. 11, 2024

(51) Int. Cl.
*A23L 27/30* (2016.01)
*C12P 19/04* (2006.01)
*C12P 19/24* (2006.01)

(52) U.S. Cl.
CPC ............... *A23L 27/33* (2016.08); *C12P 19/04* (2013.01); *C12P 19/24* (2013.01)

(58) Field of Classification Search
CPC ................................ A23L 27/33; C12P 19/24
See application file for complete search history.

(56) References Cited

U.S. PATENT DOCUMENTS

| | | | |
|---|---|---|---|
| 5,411,880 | A | 5/1995 | Izumori et al. |
| 5,679,562 | A | 10/1997 | Izumori et al. |
| 2009/0062215 | A1 | 3/2009 | Tokuda et al. |
| 2010/0204346 | A1 | 8/2010 | Okuma et al. |
| 2012/0094940 | A1 | 4/2012 | Takamine et al. |
| 2012/0244580 | A1 | 9/2012 | Hung et al. |
| 2013/0274350 | A1 | 10/2013 | Okuma et al. |
| 2014/0186925 | A1 | 7/2014 | Izumori et al. |
| 2021/0324434 | A1 | 10/2021 | Akimitsu et al. |
| 2021/0395718 | A1 | 12/2021 | Akimitsu et al. |

FOREIGN PATENT DOCUMENTS

| | | | |
|---|---|---|---|
| JP | H06-125776 | A | 5/1994 |
| JP | 2007-91696 | A | 4/2007 |
| JP | 4009720 | B2 | 11/2007 |
| JP | 2013-501519 | A | 1/2013 |
| JP | 5171249 | B2 | 3/2013 |
| JP | 5639759 | B2 | 12/2014 |
| JP | 5715046 | B2 | 5/2015 |
| JP | 5922880 | B2 | 5/2016 |
| JP | 5997693 | B2 | 9/2016 |
| JP | 2017-36276 | A | 2/2017 |
| JP | 6250946 | B2 | 12/2017 |
| WO | 2020/096006 | A1 | 5/2020 |
| WO | 2020/105709 | A1 | 5/2020 |

OTHER PUBLICATIONS

Gross, S Lee et al., "Increased consumption of refined carbohydrates and the epidemic; of type 2 diabetes in the United States: an ecologic assessment 1-3", American Society for Clinical Nutrition, 2004, vol. 79, pp. 774-779; (6 pages).

Oh, Deok-Kun, "Characterization and Structural Analysis by Agrobacterium tumefaciens d-Psicose 3-epimerase and d-Psicose Production by the enzyme", Proceedings of the 3rd Symposium of International Society of Rare Sugars, L3; (2 pages).

Matsuo, Tatsuhiro et al., "d-Psicose is a Rare Sugar That Provides No Energy to Growing Rats", J Nutr Sci Vitaminol, vol. 48, pp. 77-80, 2002; (4 pages).

Matsuo, Tatsuhiro, "Inhibitory Effects of d-Psicose on Glycemic Responses after Oral Carbohydrate Tolerance Test in Rats", J Jpn. Soc Nutr. Food Sci., 2006, vol. 59, No. 2, pp. 119-121; w/English Abstract; (3 pages).

Matsuo, Tatsuhiro et al., "Less Body Fat Accumulation with d-Psicose Diet versus D-Fructose Diet", J. Clin. Biochem. Nutr., vol. 30, pp. 55-65, 2001; (11 pages).

(Continued)

*Primary Examiner* — Jeffrey P Mornhinweg
(74) *Attorney, Agent, or Firm* — WHDA, LLP

(57) ABSTRACT

Object is to mass-produce a sweetener containing D-allulose and having a sweetness degree and taste quality very close to those of sugar at a world scale and at a low cost with price competitiveness. Provided is a mass-production method of a sweetener having functionality of D-allulose and a taste quality close to that of sugar, including acting D-allulose 3-epimerase on a D-glucose- and D-fructose-containing inexpensive composition used as a raw material, allowing isomerization of D-fructose in the raw material to proceed by an isomerization reaction between D-fructose and rare sugar D-allulose, terminating the reaction at the stage when a rare sugar D-allulose content reaches an intended content of an intended product, and thus obtaining an intended product composed of rare sugar D-allulose, D-glucose, and D-fructose, in which the D-fructose content is in a range that compensates for a weak point of D-allulose in sweetness degree and gives a taste quality close to that of sugar in cooperation with D-allulose and D-glucose.

18 Claims, 7 Drawing Sheets

Specification includes a Sequence Listing.

(56) References Cited

OTHER PUBLICATIONS

Men, Y. et al. "The development of low-calorie sugar and functional jujube food using biological transformation and fermentation coupling technology", Food Science & Nutrition., 2019, vol. 7, pp. 1302-1310; (9 pages).

Zhang, w. et al. "Production of d-allulose from d-glucose by *Escherichia coli* transformant cells co-expressing d-glucose isomerase and d-psicose 3-epimerase genes", Journal of the Science of Food and Agriculture., 2017, vol. 97, pp. 3420-3426; (7 pages).

Itoh, H. et al. "Preparation of d-psicose from d-fructose by immobilized d-tagatose 3-epimerase", Journal of Fermentation and Bioengineering., 1995, vol. 800, pp. 101-103; (3 pages).

English Translation of International Search Report dated Jun. 29, 2021, issued in counterpart Application No. PCT/ JP2021/017565. (3 pages).

SEQUENCE LISTING

```
<160> NUMBER OF SEQ ID NOS: 1

<210> SEQ ID NO 1
<211> LENGTH: 289
<212> TYPE: PRT
```

-continued

```
<213> ORGANISM: Arthrobacter histidinolovorans

<400> SEQUENCE: 1

Met Lys Ile Gly Cys His Gly Leu Val Trp Thr Gly Arg Phe Asp Ala
1               5                   10                  15

Glu Gly Ile Arg Tyr Ser Val Gln Lys Thr Lys Glu Ala Gly Phe Asp
            20                  25                  30

Leu Ile Glu Phe Pro Leu Met Asp Pro Phe Ser Phe Asp Val Ala Thr
        35                  40                  45

Ala Lys Ser Ala Leu Ala Glu His Gly Leu Thr Ala Ser Ala Ser Leu
    50                  55                  60

Gly Leu Ser Glu Ala Thr Asp Val Ser Ser Glu Asp Pro Ala Ile Val
65                  70                  75                  80

Lys Ala Gly Glu Glu Leu Leu Asn Arg Ala Leu Asp Val Leu Ala Glu
                85                  90                  95

Leu Gly Ala Thr Asp Phe Cys Gly Val Ile Tyr Ser Ala Met Lys Lys
            100                 105                 110

Tyr Met Glu Pro Ala Thr Glu Gln Gly Leu Ser Asn Ser Lys Ala Ala
        115                 120                 125

Ile Gly Arg Val Val Asp Arg Ala Ala Gly Leu Gly Ile Asn Val Ser
    130                 135                 140

Leu Glu Val Val Asn Arg Tyr Glu Thr Asn Val Leu Asn Thr Gly Arg
145                 150                 155                 160

Gln Ala Leu Ser Tyr Leu Ser Asp Val Lys Arg Pro Asn Leu Gly Val
                165                 170                 175

His Leu Asp Thr Tyr His Met Asn Ile Glu Glu Ser Asp Met Phe Ser
            180                 185                 190

Pro Val Leu Asp Thr Ala Glu Val Leu Lys Tyr Val His Ile Gly Glu
        195                 200                 205

Ser His Arg Gly Tyr Leu Gly Thr Gly Asn Val Asp Phe Asp Asn Phe
    210                 215                 220

Phe Lys Ala Leu Gly Arg Ile Gly Tyr Asp Gly Pro Val Val Phe Glu
225                 230                 235                 240

Ser Phe Ser Ser Ala Val Val Ala Pro Asp Leu Ser Arg Met Leu Gly
                245                 250                 255

Ile Trp Arg Asn Leu Trp Ala Asp Asn Glu Glu Leu Gly Ala His Ala
            260                 265                 270

Asn Ala Phe Ile Arg Asp Lys Leu Thr Ala Ile Lys Thr Ile Glu Leu
        275                 280                 285

His
```

METHOD FOR MASS-PRODUCING SWEETENER HAVING TASTE QUALITY SIMILAR TO THAT OF SUGAR AND HAVING D-ALLULOSE FUNCTIONALITY

TECHNICAL FIELD

The present invention relates to a method for mass-producing a sweetener containing three saccharides, D-glucose, D-fructose, and D-allulose (D-psicose), having the functionality of D-allulose, and having a taste quality close to that of sugar. Particularly, the invention relates to an isomerized sugar or invert sugar improvement method for converting an isomerized or invert sugar into a sweetener having the functionality of D-allulose, more specifically, a method of keeping or improving the taste quality of an inexpensive isomerized sugar or invert sugar which is a saccharide mixture containing D-glucose and D-fructose and giving it a function of exhibiting an excellent physiological effect without causing a disease by continuous intake.

BACKGROUND ART

Carbohydrates are organic compounds which are very important particularly for "Zero hunger" as an energy source for organisms and are the most abundant on earth have monosaccharides as a main constituent. These monosaccharides have typically a structure in which 3 to 8 carbon atoms are annularly connected and they can roughly be classified into two kinds, that is, an aldose and a ketose. The aldose and ketose are each classified into a triose, a tetrose, a pentose, and a hexose, depending on the number of carbon atoms. Examples of an industrially implemented reaction of the monosaccharide include a reaction of isomerizing D-glucose into D-fructose to produce an isomerized sugar. Typically, it is produced from starch such as corn starch. With an increase in the production amount of corn, an isomerized sugar has been produced in a large amount at a low cost by making use of a lot of corn starch put on the market so that it becomes considerably cheaper than that of sugar and has come to be used instead of sugar.

On the other hand, sugar which is a disaccharide, was expensive, so after isomerized high-fructose sugar became popular, it continued to be replaced by isomerized high-fructose sugar, but in 2019, approximately 180 million tons were produced, and the price has become relatively stable. By using sugar as a raw material, a good-quality sweetness of the sugar can be utilized. In addition, sugar is a disaccharide in which glucose and fructose are bound to each other so that it can be used as a supply raw material for glucose and fructose. It is therefore presumed that use of sugar may reduce a cost compared with use of an isomerized sugar, though depending on the price of sugar. Further, there is a report that a rare sugar-containing sweetener using sugar as a raw material has such an advantage that an unfavorable taste of it is less than that of a sweetener using an isomerized sugar as a raw material (Patent Document 1).

Based on such assimilable sugars, a sweetener excellent in both sweetness and physiological properties has been mass-produced industrially.

The following is a typical method for producing an isomerized sugar. First, water and a liquefying enzyme (α-amylase) are added to starch such as corn starch and the resulting mixture is hydrolyzed into dextrin at around 95° ° C. This operation is called "liquefaction". After completion of the liquefaction, the resulting liquid is cooled to about 55° C. Then, a saccharification enzyme (glucoamylase) is added to degrade the resulting mixture into small units of D-glucose, in other words, to obtain a saccharified liquid. The resulting liquefied liquid contains, as well as the D-glucose, a slight amount of an oligosaccharide. The liquid obtained by saccharification with glucoamylase is continuously passed through an immobilized enzyme, which is obtained by immobilizing, for example, an isomerizing enzyme (glucose isomerase) produced by bacteria belonging to the genus *Streptomyces* by various methods, to isomerize D-glucose into D-fructose. The aforesaid isomerization is an equilibrium reaction having an equilibrium point in the vicinity of 1 and at the time when the reaction reaches equilibrium, about 50% of D-glucose can be isomerized into D-fructose at a reaction temperature of about 60° C. To achieve such a degree of isomerization, however, a considerably long time is necessary and during heating for long hours, the reaction liquid is colored, leading to an inevitable increase in the cost in purification and concentration steps for making the product commercially available. The reaction is therefore terminated at the stage when the D-fructose content is increased to about 42% as a result of isomerization. Then, purification and concentration are performed to obtain a glucose fructose syrup having a fructose content of 42%.

The enzymes used for producing them are each produced by a safe microorganism. Described specifically, an isomerization reaction of D-glucose into D-fructose with the aid of glucose isomerase is an equilibrium reaction and a D-glucose:D-fructose ratio of the isomerized sugar is usually about 58:42. The sweetness degree of the glucose fructose syrup having a D-fructose content of 42% is 70 to 90 assuming that the sweetness degree (sweetness intensity) of sugar is 100.

Further, a glucose fructose syrup having a fructose content of 55% can be produced using chromatography as a separation apparatus. Described specifically, the aforesaid 42% isomerized sugar is converted into a 55% isomerized sugar as follows: First, a D-fructose syrup having a D-fructose content of about 95% is obtained by continuous saccharide separation with a large-scale apparatus such as a reaction tower packed with a cation exchange resin and then, the resulting D-fructose syrup is mixed with the aforesaid 42% isomerized sugar. Alternatively, purified D-fructose may be added in order to eliminate sweetness shortage. In each case, a final D-glucose:D-fructose ratio is usually about 45:55.

The sweetness degree of the resulting fructose glucose syrup having a D-fructose content of 55% is 100 to 120 assuming that the sweetness degree (sweetness intensity) of sugar is 100.

The sweetness degree (sweetness intensity) of D-glucose is 65 to 80 and that of D-fructose is 120 to 170 assuming that the sweetness degree of sugar is 100. Although the intensity of the sweetness degree is higher in the following order: D-fructose (fructose)>sucrose (sugar)>D-glucose (glucose), the sweetness degree of the isomerized sugar largely depends on a temperature because the sweetness of D-fructose is 60% of sucrose at high temperatures, is equal thereto at 40° C., and is higher than that of sucrose at a temperature therebelow.

Due to appearance of the chromatographic fructose concentrating technology in the late 1970s, an isomerized sugar can be mass-produced. As it has become popular rapidly, a consumption amount of the isomerized sugar increases, causing a reduction in the consumption amount of sugar. Thus, the isomerized sugar has taken the place of sugar. A high fructose corn syrup (HFCS) 55 having a D-fructose content of 55% and a D-glucose content of 42% and having sweetness adjusted to be equal to that of sucrose is used for soft drinks and thus, is most popular as if it is considered to be new sugar.

An isomerized sugar or invert sugar which is a saccharide mixture composed mainly of D-glucose and D-fructose has been used more widely due to its economical merit, but in developed countries such as the United States and Japan, it is suspected as a cause of hyperglycemia or overweight (obesity) ("metabolic syndrome") (Non-Patent Document 1). Since the metabolism of D-fructose in the liver easily accelerates lipogenesis and easily induces hyperlipidemia or obesity compared with that of D-glucose, an attention has been paid to the relation between an intake amount of D-fructose contained in a fructose glucose syrup and an increase in the number of obese subjects (lifestyle-related disease).

As described above, the sweetness degree or sweetness quality of the isomerized sugar is different from that of widely used sugar and it has been tried to produce an isomerized sugar having a sweetness degree or sweetness quality close to that of sugar by changing a D-glucose: fructose ratio. It is however impossible to say that a satisfactory one has been established.

Some developments are underway for putting a sweetener excellent in sweetness and physiological properties and not causing the aforesaid diseases on the market based on these assimilable sugars which are very important for organisms as an energy source or the like.

For the improvement of the function of the assimilable sugars, D-allulose which are energy zero and have various functionalities have attracted attentions.

D-allulose is one of rare sugars and is produced in a yield of 20 to 25% by acting D-ketohexose 3-epimerase (Patent Document 2) on D-fructose. It is reported that D-allulose is produced in a yield of 40% by using D-allulose 3-epimerase (Non-patent Document 2).

Pure rare sugar D-allulose (=D-psicose) can be produced, for example, by using ketose 3-epimerase (for example, D-allulose 3-epimerase) and, as a raw material, D-fructose. With regard to rare sugar D-allulose, powder crystals of D-allulose can be produced by acting epimerase on D-fructose to prepare a mixture of D-fructose and D-allulose, followed by separation and purification. It has been made clear that D-allulose exhibits qualities as a material for preventing lifestyle-related diseases such as zero kilo calories (Non-patent Document 3), a postprandial blood sugar level inhibitory effect (Non-Patent Document 4), an effect of inhibiting a sharp blood sugar level increase due to D-glucose which is taken via a food and a beverage and constitutes a digestive sugar (Patent Document 3), and an anti-obesity effect (Non-patent Document 5).

This D-allulose itself is used as a sweetener, a pharmaceutical, or the like and mass production and sales of it have been started around the world. This D-allulose is energy zero and has various functionalities so that in particular, the sale as a sweetener leads the way. When D-allulose is produced after production of purified D-fructose, different steps are required for them so that at present, there are many economic problems to solve in the industrial mass production of D-allulose due to limitations in raw materials, transport, a reaction cost, or a plant management cost.

Rare sugar D-allulose is also called "D-psicose", is an epimer of D-fructose, and is similar to D-fructose in the quality of sweetness. The sweetness degree of it is however about 70% of that of sugar and is required to be brought closer to that of sugar. Technologies of mixing an isomerized sugar with rare sugar D-allulose which exhibits, when taken with a food and a beverage, an effect of inhibiting a sudden blood sugar level rise due to D-glucose constituting a digestive sugar contained in them have been developed.

The first one is production of a rare sugar sweet (RSS), that is, a rare-sugar-containing syrup by using an isomerized sugar as a raw material and making use of a chemical reaction (by treating it in a system having therein at least one selected from the group consisting of basic ion exchange resins, alkalis, and calcium salts) (Patent Document 4). It is a syrup containing, in addition to main ingredients D-glucose and D-fructose, about 15% of a rare sugar (5.4% of D-allulose, 2.0% of D-tagatose, and 1.4% of D-allose).

The second one is to obtain a sweetener having a sweetness degree and taste quality very close to those of sugar by overcoming the problems of the sweetness of the conventional sweetener, fructose-glucose liquid sugar, and its differences from sugar.

Developed is a sweetener having a sweetness degree and taste quality almost similar to those of sugar composed of D-fructose, D-glucose, and D-allulose and at the same time, is a sweetener for suppressing an obesity effect of an isomerized sugar. It has 9 parts by weight or more of D-allulose based on a total of 100 parts by weight of D-glucose and D-allulose, has 34 to 55 parts by weight of D-fructose based on a total of 100 parts by weight of D-fructose, D-glucose and D-allulose, and has a total of 66 to 45 parts by weight of D-glucose and D-allulose based on a total of 100 parts by weight of D-fructose, D-glucose and D-allulose (Patent Document 5).

PRIOR ART DOCUMENTS

Patent Documents

Patent Document 1: Japanese Patent No. 6250946
Patent Document 2: Japanese Laid-Open Patent Publication No. 1994-125776
Patent Document 3: Japanese Patent No. 5171249
Patent Document 4: Japanese Patent No. 5715046
Patent Document 5: Japanese Patent No. 5639759
Patent Document 6: Japanese Patent No. 5997693
Patent Document 7: Japanese Patent No. 5922880
Patent Document 8: Japanese Laid-Open Patent Publication No. 2017-36276
Patent Document 9: Japanese Patent No. 4009720
Patent Document 10: Japanese Laid-Open Patent Publication No. 2007-91696

Non-Patent Documents

Non-Patent Document 1: Am. J. Clin. Nutr., 2004, 79, 774-9.
Non-Patent Document 2: The 3rd Symposium of International Society of Rare Sugars.
Non-Patent Document 3: J. Nutr. Sci. Vitaminol., 48, 77-80.
Non-Patent Document 4: J. Nutr. Sci. Vitaminol., 59, 191-121.
Non-Patent Document 5: J. Clin. Biochem. Nutr., 30, 55-65.

SUMMARY

Technical Problem

The intended product produced by the aforesaid two methods is an isomerized sugar that exhibits an excellent physiological effect, but it does not have sufficient price competitiveness for world scale mass-production. The problem is how to reduce the cost of it. Since a new problem of reducing $CO_2$ emission is before us these days, it is presumed that $CO_2$ emission is a costly burden and increases its weight in the cost structure. There is therefore a demand for the development of a new production process that enables a reduction in $CO_2$ emission. Creation of a new globally competitive production process that efficiently achieves principally possible "craftsmanship" by the aforesaid two methods is presumed to lead to a cost reduction having a huge impact.

Corn and sugarcane have ideal qualities as biomass. With an increase in the production amount of corn, a large amount of corn starch has been put on the market and a large amount of isomerized sugars are produced therefrom at low cost. Then, the isomerized sugars become very cheaper than sugar and therefore have come to take the place of sugar. It is however presumed that stable supply of corn to isomerized sugars can be achieved only by improvement in the isomerized sugars.

The reason is as follows. An alcohol is made from corn starch or syrup and the bioethanol is subjected to a dehydration reaction to produce ethylene. Thus, so-called biomass-derived polyethylene is produced in large quantities. A world polyethylene price is determined based on high-cost naphtha so that bio-polyethylene is presumed to have price competitiveness with fossil-fuel based polyethylene. The greenhouse gas reduction effect of bio-polyethylene is one-fifth that of petroleum-derived polyethylene on price. Bio-polyethylene can appeal to consumers that it uses a material friendly to the earth warming and therefore, whole or part of fossil fuel-based polyethylene has been replaced by it. Due to a sudden increase in the demand for corn by ethanol, a steep price rise may be caused by shortage of corn. There is no guarantee that corn can be supplied as a raw material for such a large amount of isomerized sugars that exceeds the present amount required for "Zero hunger".

All the harvested sugarcane is collected in a sugar factory and is processed into sugar there. The collection system which is the biggest problem when using biomass has already been established. Compared with other crops, sugarcane has an unparalleled great advantage in its productivity and versatility. Now, biomass has attracted attentions as part of global warming countermeasures and ethanol production has been carried out using sugarcane. Thus, sugarcane is becoming a trump card for global warming countermeasures because of high biomass productivity. There is therefore concern about a steep rise in the price of sugarcane due to shortage, similar to that of corn starch.

The problem of an isomerized sugar or invert sugar is that continuous intake of it may cause a lifestyle-related disease such as obesity. In the isomerized sugar, D-fructose, which is a constituent thereof, shows more intense sweetness at a lower temperature so that about 70% of the whole consumption amount of it is added to a beverage such as refreshing drink and the other portion is used for food in general. Now that we can easily get even excessive sweetness derived from an assimilable sugar, a carbohydrate (assimilable sugar) typified by sugar or an isomerized sugar has been regarded problematic recently because it is accompanied with diabetes or obesity. A sweetener cannot be supplied for energy source for "Zero hunger" unless it is based on such an assimilable sugar, has excellent sweetness, and does not cause such a disease.

More specifically, there is a demand for a method of mass-producing, at a price-competitive low cost and in a world scale, a sweetener that contains D-allulose effective for suppressing a sudden blood sugar level increase due to D-glucose constituting a digestive sugar taken through food or beverages and has a sweetness degree and a taste quality very close to those of sugar. Another object of the present invention is to provide a food and beverage, a pharmaceutical or quasi-drug, and a cosmetic that are produced at a low cost, contain D-allulose, are excellent in sweetness, and do not cause a disease even after long-term intake.

Solution to Problem

The present inventors thought of, in studying rare sugars while producing D-allulose and paying attention only to the effectiveness thereof, circulation from glucose which is a monosaccharide $C_6H_{12}O_6$ obtained from a plant as a result of photosynthesis using the energy of sun light to a starch which is a polymerization product of glucose and then to a disaccharide of glucose and fructose in the flow of energy toward human beings. A saccharide has an important role as an energy source and is essential for human beings and organisms, but it has many problems to solve. This glucose which is familiar with us is however used after converted into an isomerized sugar by the aid of an isomerase such as D-xylose isomerase (glucose isomerase) and sugar is used after converted into glucose and fructose by the aid of invertase. Its use has been started as not only a sweetener but also as many inexpensive raw materials in an organic chemistry field. The present inventors have found that when an isomerized sugar and sugar (invert sugar) are supplied at a low cost and ordinarily used in the world and the global trend and the large problem faced by human beings are recognized, the effectiveness of a rare sugar will be useful. The present inventors have convinced that D-allulose will become a rare sugar whose production is started all over the world for solving the problems of an isomerized sugar or sugar.

Combination of the effectiveness of D-allulose with inexpensiveness of an isomerized sugar or sugar (invert sugar) was achieved by ketose 3-epimerase (for example, Patent Document 6, PCT/JP2019/045672)) which is an enzyme familiar with the present inventors. In a new sugar industry where production has been performed with fructose already popular in a global level as a raw material, an inexpensive isomerized sugar or sugar (invert sugar) can be produced as a valuable composition at the level of a researcher by making full use of ketose 3-epimerase, which is familiar with the present inventors.

In other words, an intended product can be mass-produced at a low cost by producing glucose, fructose, and D-allulose at an appropriate ratio. Because of the problems of an isomerized sugar, sugar, or the like such as obesity, recognition of the importance of them as an energy source for human beings is declining. In the present social situations, therefore, they are more frequently used as bioethanol or the like at a low cost. In order to overcome such an important problem relating to a carbohydrate, the power of biotechnology (ketose 3-epimerase) is used to overcome the problems of these saccharides and convert them into a carbohydrate appropriate for human beings as an energy source. The present invention is an invention leading to "Zero hunger".

Ketose 3-epimerase converts D-fructose into D-allulose having functionality. In the present invention, any carbohydrate containing D-fructose as a raw material can be used as a raw material. Typical examples include isomerized sugars and invert sugars. They are each composed of D-glucose, D-fructose, and D-allulose and a saccharide having an expected composition can be produced only by the aid of ketose 3-epimerase. The present inventors have found a considerably simple process, in which the isomerization of glucose and hydrolysis of sugar are conducted using a system already used in a plant for large-scale production and a bioreactor only for ketose 3-epimerase is added newly to the system. The present invention has been completed based on a concept (=creation of a new production process) of embracing, in the present invention, a reaction performed in the sugar industry.

To enhance the cost performance of this new production process, the present inventors have paid attention to high durability (long life span) of the enzyme ketose 3-epimerase. Paying attention to the strains which were approved for use and listed as a food not only in Japan but also Europe and the United States, and had almost no toxicity, the present inventors sampled soils from various locations, separated microorganisms therefrom, and continued to search for a microorganism having ketose 3-epimerase activity. As a result, they found a new microorganism producing ketose 3-epimerase from many isolated strains. The strain is *Arthrobacter histidinolovorans* Y586-1 which is a microorganism belonging to the genus *Arthrobacter*. It had high activity and produced highly heat-resistant and novel ketose 3-epimerase so that the present inventors filed an international application for it separately [PCT/JP2019/045672 (international filing date: Nov. 21, 2019)]. They have convinced that the high heat resistance and high productivity of it will promise the total productivity derived from not activity but high durability (long life span) of the enzyme.

Details are as described above and in short, the present inventors have proceeded with intensive research with a view to overcoming the problems. During the research, (A) they have recognized that a sweetener containing D-glucose, D-fructose, and D-allulose has the following characteristics: (i) D-glucose is important as an energy source, (ii) D-fructose has an important role of giving sweetness and it gives a taste quality close to that of sugar as well as D-glucose, but has a problem as a saccharide such as causing obesity by long-term continuous intake, and (iii) D-allulose has a physiological function against obesity.

Based on the aforesaid recognition, (B) the present inventors have found that an inexpensive sweetener having a composition suited for an intended purpose can be provided by adjusting the composition of the three saccharides to an appropriate one.

The present inventors have thought that an inexpensive raw material containing D-fructose is necessary for the production of D-allulose; and with respect to the inexpensive raw material containing D-fructose, (i) D-fructose can easily be produced from D-glucose with the aid of D-xylose isomerase so that D-glucose produced from starch can be used, (ii) inexpensive isomerized sugars having various compositions are put on the market as D-glucose+D-fructose and they will be a raw material, and (iii) sugar is an inexpensive sweetener in which D-glucose and D-fructose are bound to each other and it is easily degraded by invertase so that it will be an inexpensive raw material also usable for bioethanol production. Based on the aforesaid findings (i) to (iii) about the raw material for production, the raw material for production may be D-glucose or D-fructose so that decided is use of various isomerized sugars (which can be produced only by epimerase columns and a product having an expected composition can be produced by using them properly) for which mass production technology has been established and inexpensive sugar (that produced and used much for bioethanol and having a 1:1 composition of D-glucose and D-fructose can be used at a low cost). When such raw materials are used for production, a product not containing a side-reaction product and therefore in pure form can be produced by connecting a conventional production line in an appropriate form and addition of an extra purification step is not required.

And, (C) by using an enzyme reaction in which high heat-resistance and high-productivity D-allulose 3-epimerase is acted on the raw material to realize total productivity derived from the high durability (long life span) of the enzyme and at the same time, producing without using a simulated moving bed chromatography, world-wide scale mass production with sufficient price competitiveness can be performed, leading to the completion of the present invention.

The gist of the present invention is a method described below in (1) to (10) for mass-producing a sweetener having functionality of D-allulose and having a taste quality close to that of sugar.

(1) A method for mass-producing a sweetener containing three saccharides D-glucose, D-fructose, and D-allulose, having functionality of D-allulose, and having a taste quality close to that of sugar, including:

using, as a raw material, an inexpensive composition containing D-glucose and D-fructose, acting D-allulose 3-epimerase on the raw material to allow isomerization of D-fructose therein to proceed by an isomerization reaction between D-fructose and rare sugar D-allulose, terminating the reaction at a stage when a rare sugar D-allulose content reaches an intended content of an intended product, and obtaining the intended product having, in a composition of rare sugar D-allulose, D-glucose, and D-fructose, a D-fructose content in a range that compensates for a weak point of D-allulose in low sweetness degree and gives the intended product a taste quality close to that of sugar in cooperation with D-allulose and D-glucose.

(2) The method as described above in (1), wherein contents of individual ingredients are determined to obtain an appropriate composition suited for a purpose after consideration of the following respective characteristics of the ingredients:

D-glucose is important as an energy source in the intended product and has a sweetness intensity of 65 to 80 assuming that a sweetness intensity of sugar is 100;

D-fructose has a sweetness intensity of 120 to 170, is important for giving sweetness, and gives a taste quality close to that of sugar in cooperation with D-allulose and D-glucose, but has a problem as a saccharide that causes obesity by continuous intake; and D-allulose has a sweetness intensity of 70 and is capable of giving such physiological functions as obesity prevention and suppression of a sudden blood sugar level rise caused by digestive sugar.

(3) The method as described above in (1) or (2), wherein the raw material is a composition containing D-glucose and D-fructose and produced by acting D-xylose isomerase on D-glucose produced from starch and allowing isomerization to proceed by an equilibrium reaction between D-glucose and D-fructose or produced by acting invertase on sugar to degrade the sugar.

(4) The method as described above in any of (1) to (3), wherein the raw material is an inexpensive isomerized sugar or invert sugar and the intended product is an improved isomerized sugar or invert sugar having functionality of D-allulose, having a taste quality close to that of sugar, and exhibiting an excellent physiological effect without causing a disease by continuous intake.

(5) The method as described above in (4), wherein a glucose fructose syrup and/or a fructose glucose syrup is used as the inexpensive isomerized sugar as the raw material.

(6) The method as described above in any of (1) to (5), wherein the rare sugar D-allulose content of the intended product is attained by adjusting an enzyme activity of the D-allulose 3-epimerase used.

(7) The method as described above in any of (1) to (6), wherein the isomerization reaction is performed by passing a substrate solution through an immobilized enzyme column and the intended product having an intended composition is obtained by adjusting at least one selected from the group consisting of a flow rate of the substrate, a reaction time with the substrate, a reaction temperature, pH of the substrate solution, and an amount of the enzyme.

(8) The method as described above in any of (1) to (7), wherein a 100% intended product is obtained using an immobilized enzyme reaction with the raw material as a substrate without producing a by-product theoretically.

(9) The method as described above in any of (1) to (8), wherein the intended product is not lost in a separation operation by simulated moving bed chromatography during the production steps.

(10) The method as described above in any of (1) to (9), further comprising, after acting the D-allulose 3-epimerase on the raw material to allow isomerization of D-fructose therein to proceed by an isomerization reaction between D-fructose and rare sugar D-allulose and terminating the reaction at a stage when a rare sugar D-allulose content reaches an intended content of an intended product, a reaction step for acting D-xylose isomerase which is inert to rare sugar D-psicose on the reaction product to allow isomerization to proceed by an equilibrium reaction between D-fructose and D-glucose.

(11) The method as described above in (10), wherein a high fructose syrup is used as the inexpensive isomerized sugar as the raw material.

(12) The method as described above in any of (1) to (11), which is an industrially-practicable and low-cost production method based on total productivity derived from high heat resistance of the D-allulose 3-epimerase used and high durability (long life span) of the enzyme as a result thereof.

Advantageous Effects of Invention

The present invention makes it possible to provide an improvement method for imparting an isomerized sugar or invert sugar which is a saccharide mixture composed mainly of D-glucose and D-fructose with a function of exhibiting an excellent physiological effect without causing a disease by continuous intake while keeping or improving the original taste quality.

D-fructose (fructose) has the advantage of being sweet and delicious but has the disadvantage of having an adverse effect on accumulation of a neutral fat or the like after long-term continuous intake so that an isomerized sugar containing it is said to be a cause of obesity or the like. It is possible to obtain a new sweetener which has a D-fructose content adjusted to prevent appearance of the disadvantage caused by long-term continuous intake, has a composition adjusted to bring out the advantage of D-fructose in sweetness, compensates for the disadvantage of D-allulose, that is, low sweetness degree, and having functionality of D-allulose. The rare sugar-containing composition of the present invention having a taste quality similar to that of sugar is composed of D-glucose, D-fructose, and D-allulose so that it can be used not only for food and beverages, particularly, functional food (for obesity prevention, or the like) but also for pharmaceuticals, cosmetics, feeds, agricultural chemicals (plant growth regulators, plant disease resistance amplifiers, and the like), and industrial uses.

According to the present invention, it is possible to provide a method for mass-producing a sweetener having the functionality of D-allulose and having a taste quality close to that of sugar in a convenient matter without an additional step only by using raw materials and one enzyme reaction, adding a second enzyme reaction if necessary, and/or adding an enzyme reaction to a raw material production if necessary. The production method is characterized by that it does not need a new equipment investment cost, the production is completed by reacting an epimerase and if necessary, isomerase under respectively suited conditions, production can be performed while using continuous or individual reactions freely, and total productivity derived from high durability (long life span) of the enzyme is achieved.

For the production of a conventional carbohydrate sweetener such as HFCS or D-allulose, a separation operation by simulated moving bed chromatography is essential. In the present invention, the whole mixed syrup as a raw material can be theoretically converted into a product in a yield of 100% without this separation operation.

In addition, a sweetness degree similar to that of sugar can be attained by the adjustment of a D-fructose content and a production cost can be reduced by connecting a conventional production line in an appropriate form, making it possible to provide a production method completed by constructing a system which has never existed and in which the function of D-allulose is kept sufficiently.

Since a separation operation is omitted, almost no reduction in concentration due to the separation occurs, a concentrating operation can be omitted, and a product can be obtained only by deionization operation and concentration of an enzyme reaction product. A significant cost reduction can therefore be expected. All the merits of the production method already established for isomerized sugars or invert sugars can be enjoyed. In addition, a method for mass-producing a sweetener—containing D-allulose effective for suppressing a sudden blood sugar level rise due to D-glucose which is taken through food and beverages and constitutes a digestive sugar and having a sweetness degree and a taste quality very close to those of sugar—at a low cost with price competitiveness and on a global scale can be provided only by adding the most inexpensive step.

DESCRIPTION OF EMBODIMENTS

[Raw Material for Production]

As a raw material, an inexpensive one is necessary. To enable world scale mass production with sufficient price competitiveness, a raw material used is required to be inexpensive and responsive to mass production.

In order to obtain three saccharides D-glucose, D-fructose, and D-allulose at low cost, any inexpensive saccharide containing D-glucose or D-fructose is usable as a raw material (refer to FIGS. 1 to 5).

For the preparation of D-allulose, D-allulose can be obtained from D-fructose so that it should be made from an inexpensive raw material containing D-fructose. The following are examples of the inexpensive raw material.

Figure 1:
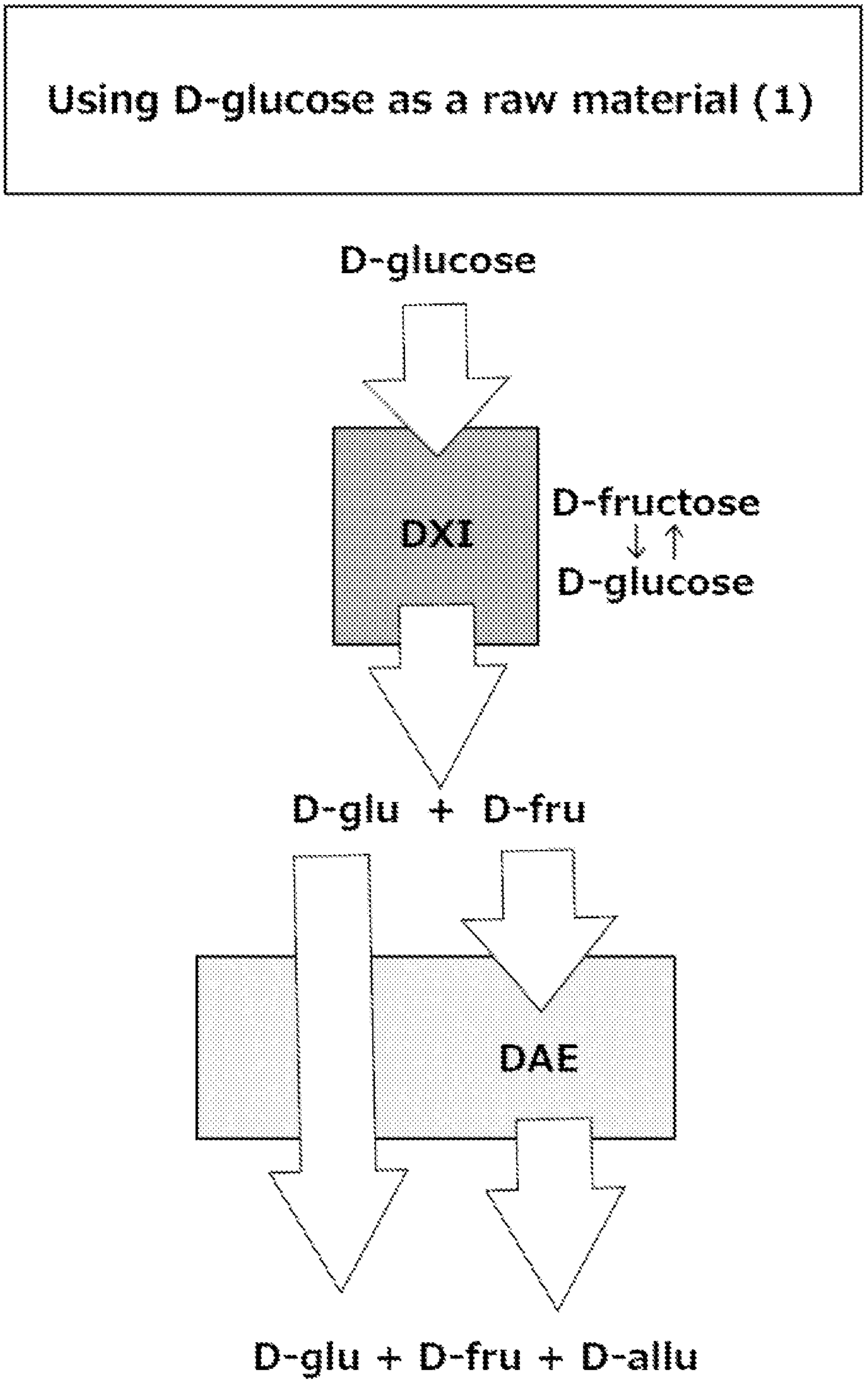
FIG. 1 is a view for describing a production method (1) using D-glucose as a raw material and it is a method for obtaining an intended product composed of rare sugar D-allulose, D-glucose, and D-fructose by using, as a raw material, a composition (isomerized sugar) containing D-glucose and D-fructose produced (=produced by a typical production method of an isomerized sugar) by acting D-xylose isomerase (DXI) on D-glucose produced from starch and allowing isomerization to proceed by an equilibrium reaction between D-glucose and D-fructose, acting D-allulose 3-epimerase (DAE) on the composition to allow isomerization to proceed by an equilibrium reaction between D-fructose and rare sugar D-allulose, which reaction is for isomerizing D-fructose in the raw material into rare sugar D-allulose, and terminating the reaction at the stage when a rare sugar D-allulose content reaches an intended content of the intended product.
Figure 2:
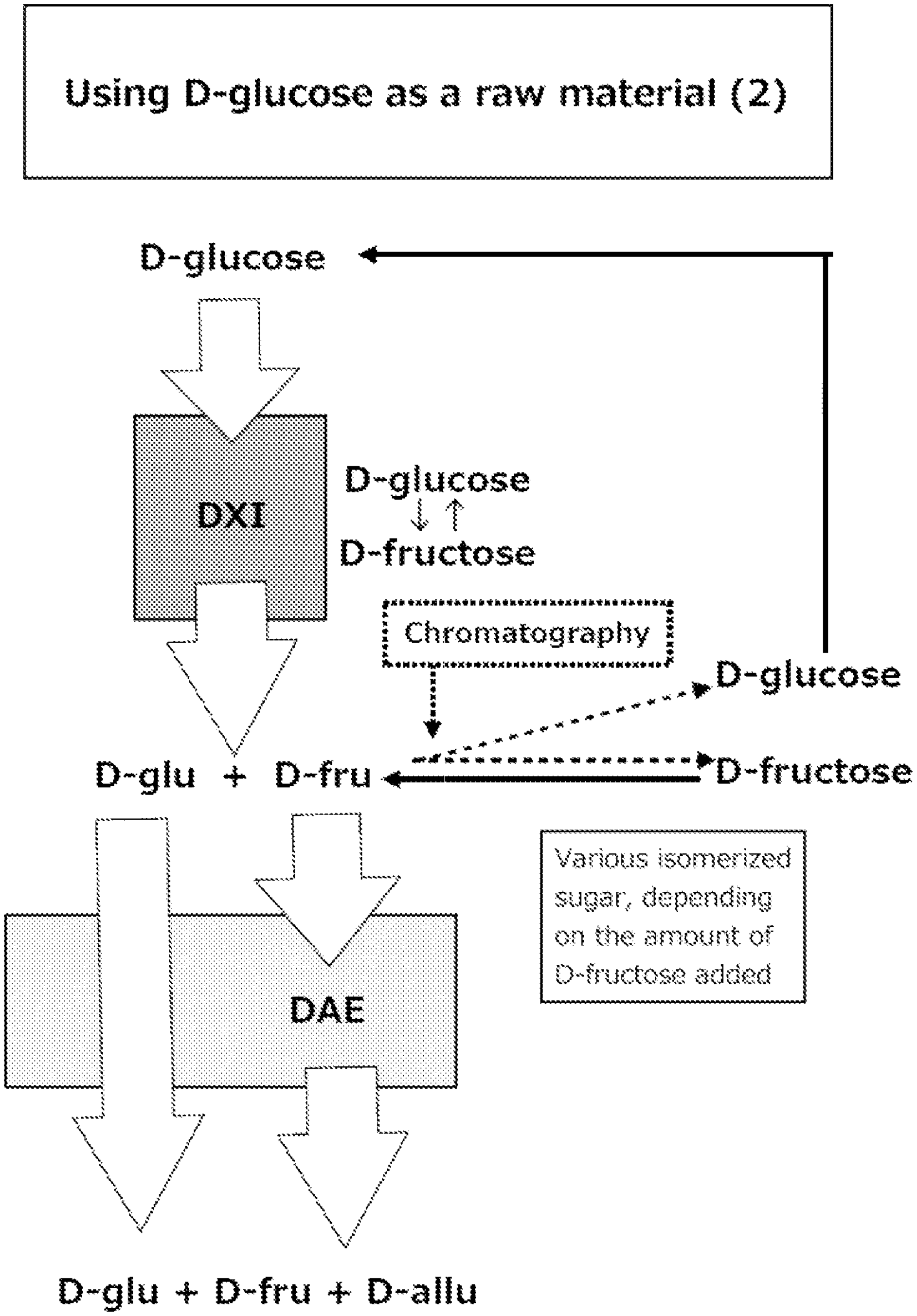
FIG. 2 is a view for describing a production method (2) using D-glucose as a raw material and it is a method for obtaining an intended product by separating a composition (isomerized sugar) produced by a typical isomerized sugar production method and containing D-glucose and D-fructose with chromatography as a separation apparatus into D-glucose and D-fructose to obtain a D-fructose liquid first, mixing the resulting D-fructose liquid with the isomerized sugar to prepare various isomerized sugars different in the addition amount of D-fructose, and acting DAE on the resulting isomerized sugars used as a raw material to allow isomerization of them to proceed by an equilibrium reaction between D-fructose and rare sugar D-allulose which reaction is for isomerizing D-fructose in the raw material into rare sugar D-allulose.

<1> D-fructose can be produced easily from D-glucose with the aid of D-xylose isomerase so that D-glucose obtained from starch can be used (refer to FIGS. 1 and 2).

For example, in an example of using D-glucose as a raw material, an intended product composed of rare sugar D-allulose, D-glucose, and D-fructose can be obtained by using, as a raw material, a composition (isomerized sugar) containing D-glucose and D-fructose obtained by (=produced by a typical production method of an isomerized sugar) acting D-xylose isomerase (DXI) on D-glucose produced from starch to allow isomerization to proceed by an equilibrium reaction between D-glucose and D-fructose, acting D-allulose 3-epimerase (DAE) on the raw material to allow isomerization to proceed by an equilibrium reaction between D-fructose and rare sugar D-allulose, which reaction is for isomerizing D-fructose in the raw material into rare sugar D-allulose, and terminating the reaction at the stage when a rare sugar D-allulose content reaches an intended content of the intended product (FIG. 1).

In another example using D-glucose as a raw material, an intended product can be obtained by separating a composition (isomerized sugar), which is produced by a typical isomerized sugar production method and contains D-glucose and D-fructose, into D-glucose and D-fructose with chromatography as a separation apparatus to obtain a D-fructose liquid first, mixing the resulting D-fructose liquid with the isomerized sugar to prepare various isomerized sugars different in the addition amount of D-fructose, acting DAE on the resulting isomerized sugars used as a raw material to allow isomerization to proceed by an equilibrium reaction between D-fructose and rare sugar D-allulose which reaction is for isomerizing D-fructose in the raw material into rare sugar D-allulose (FIG. 2).

<2> Isomerized sugars for which a production method at a low cost has been established are commercially available at a low cost as various compositions as a D-glucose and D-fructose mixture and they are usable as raw materials.

Figure 3:
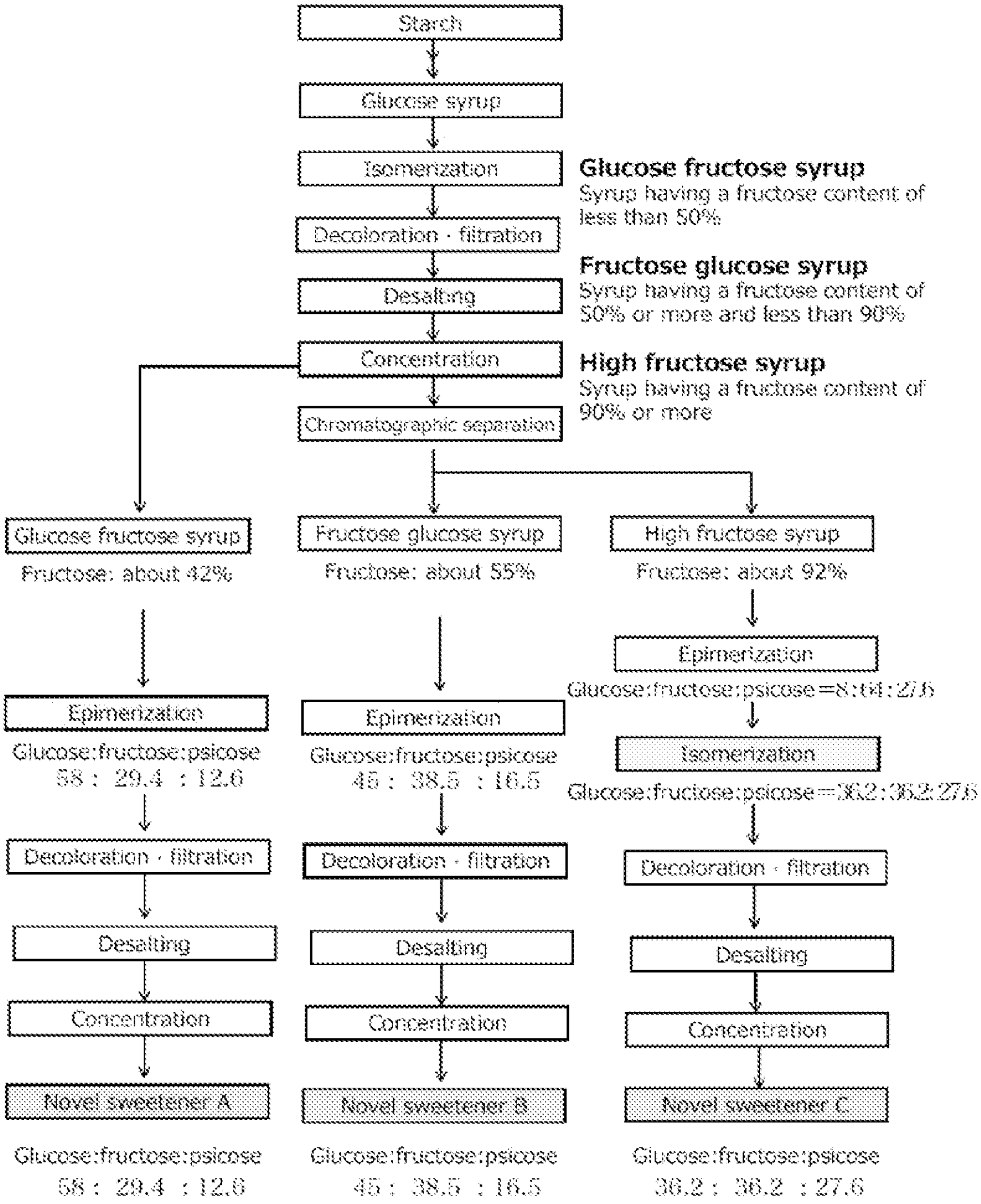
FIG. 3 is a view for describing production steps of various isomerized sugars (glucose fructose syrup, fructose glucose syrup, high fructose syrup) of Japanese Agricultural Standards and a method for obtaining an intended product by acting DAE on the resulting various isomerized sugars used as a raw material and allowing isomerization to proceed by an equilibrium reaction between D-fructose and rare sugar D-allulose which reaction is for isomerizing D-fructose in the raw material into rare sugar D-allulose. It is to be noted that the production method similar to that of FIG. 1 is shown on the left side; the production method similar to that of FIG. 2 is shown on the center, and a production method using high fructose syrup as a raw material is shown on the right side. Shown is a method, similar to the separately applied production method (FIG. 4) (PCT/JP2019/043722), of acting the aforesaid D-allulose 3-epimerase on the raw material to allow isomerization of D-fructose therein to proceed by an isomerization reaction between D-fructose and rare sugar D-allulose, terminating the reaction at the stage when the rare sugar D-allulose content reaches an intended content of an intended product, and then adding a reaction step of acting D-xylose isomerase inert to rare sugar D-psicose on the reaction product to allow isomerization to proceed by an equilibrium reaction between D-fructose and D-glucose and thereby adjusting a D-fructose content to an intended content of the intended product.
Figure 4:
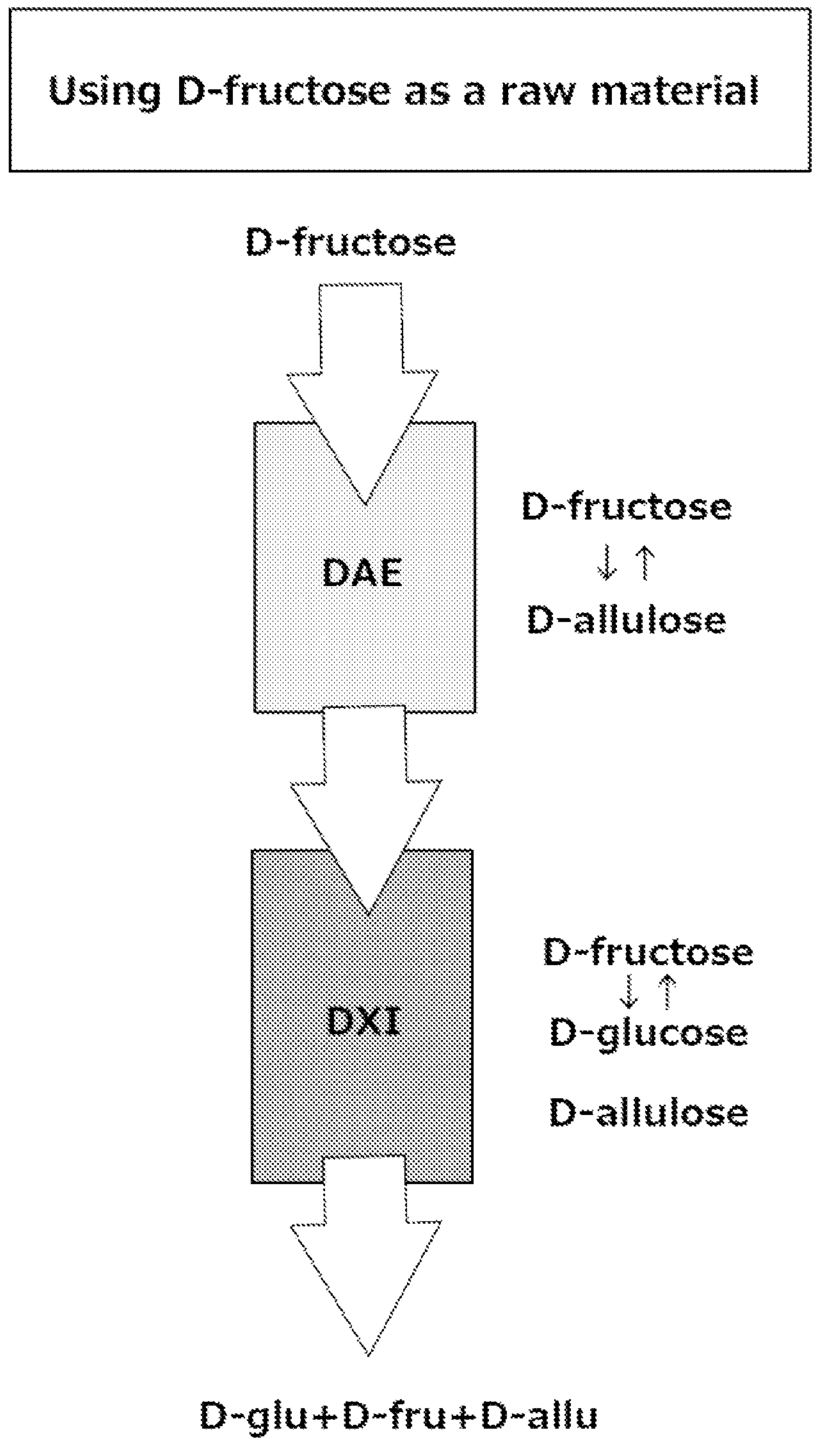
FIG. 4 is a view for describing the separately applied production method using D-fructose as a raw material (PCT/JP2019/043722), which includes a first stage of converting D-fructose into a mixture with D-allulose with the aid of ketose 3-epimerase (DAE) and a second stage of converting D-fructose into D-glucose with the aid of D-xylose isomerase (DXI) inert to D-allulose to obtain an intended product having a new composition of D-glucose, D-fructose, and D-allulose.
Figure 5:
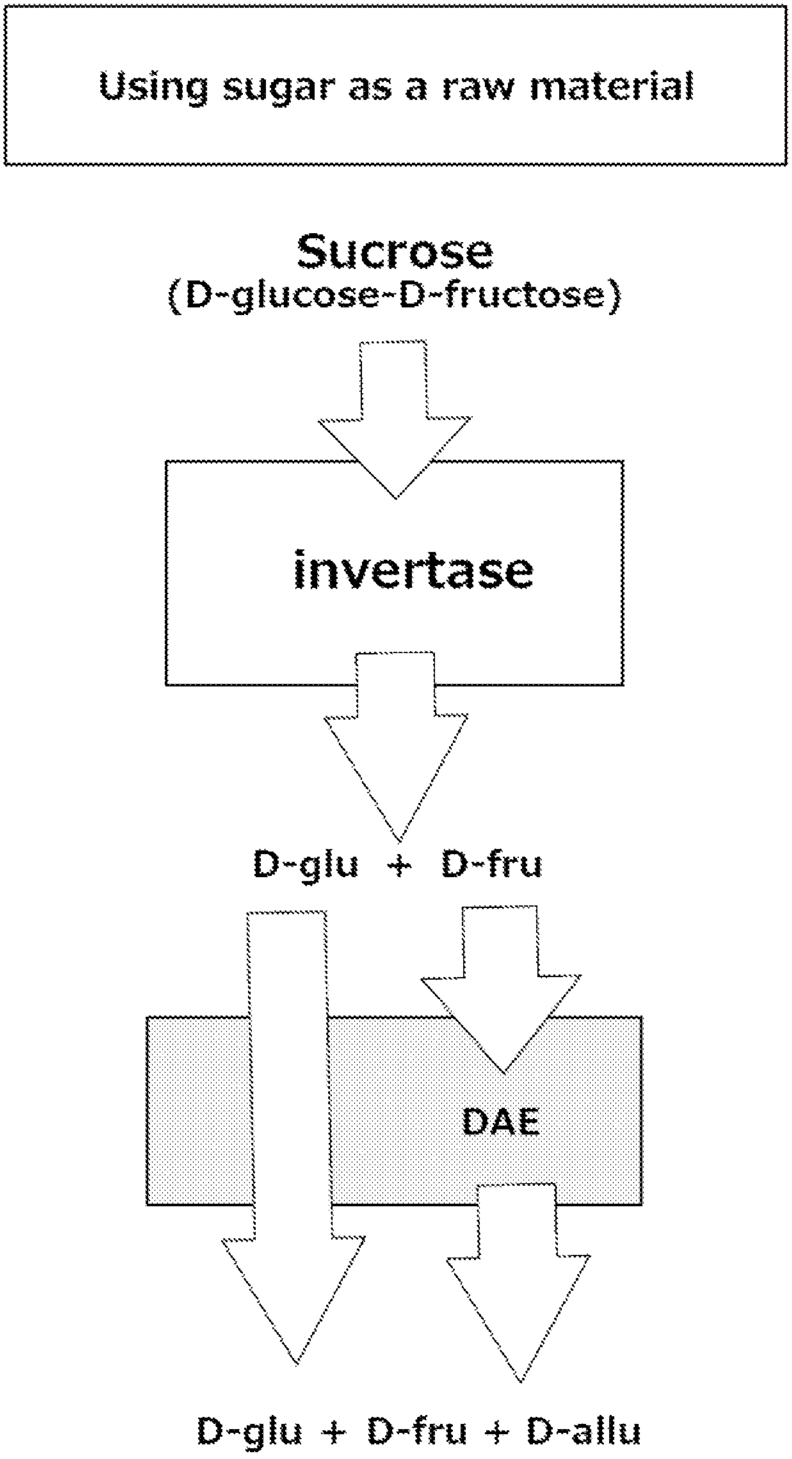
FIG. 5 is a view for describing a production method using sugar as a raw material, which includes acting invertase on sugar to degrade it and thus produce a composition having D-glucose and D-fructose as main components (produced by a typical production method of an invert sugar), acting D-allulose 3-epimerase (DAE) on the resulting composition used as a raw material to allow isomerization to proceed by an equilibrium reaction between D-fructose and rare sugar D-allulose, which reaction is for isomerizing D-fructose in the raw material into rare sugar D-allulose, and terminating the reaction at the stage when a rare sugar D-allulose content reaches an intended content of the intended product to obtain an intended product composed of rare sugar D-allulose, D-glucose, and D-fructose.

In FIG. 3, described are production steps of various isomerized sugars (glucose fructose syrup, fructose glucose syrup, and high fructose syrup) of Japanese Agricultural Standards and a method for obtaining an intended product by acting DAE on the resulting various isomerized sugars used as a raw material and allowing isomerization to proceed by an equilibrium reaction between D-fructose and rare sugar D-allulose which reaction is for isomerizing D-fructose in the raw material into rare sugar D-allulose. In this figure, shown on the left side is the production method similar to that of FIG. 1 using a glucose fructose syrup having a fructose content of about 42% as a raw material; shown on the center is the production method similar to that of FIG. 2 using a fructose glucose syrup having a fructose content of about 55% as a raw material; and shown on the right side is the production method using a high fructose syrup having a fructose content of about 92%. When it is necessary to adjust a D-fructose content in the intended product so as to be in the optimum range to present a taste quality equal to that of sugar and so as to prevent appearance of the disadvantage of long-term continuous intake, D-fructose should be converted into D-glucose. A production method adopted as needed includes acting D-allulose 3-epimerase on the raw material to allow isomerization of D-fructose therein by an isomerization reaction between D-fructose and rare sugar D-allulose, terminating the reaction at the stage when a rare sugar D-allulose content reaches an intended content of the intended product, and then adding a reaction step for acting D-xylose isomerase inert to rare sugar D-psicose to allow isomerization to proceed by an equilibrium reaction between D-fructose and D-glucose, and thereby adjusting a D-fructose content to an intended content of the intended product. Such a two-step production method is similar to the production method (FIG. 4) separately applied (PCT/JP2019/043722) and using D-fructose as a raw material. In FIG. 4, shown is the aforesaid separately applied method using D-fructose as a raw material, which includes a first step of converting D-fructose into a mixture with D-allulose with the aid of ketose 3-epimerase (DAE) and a second step of converting D-fructose into D-glucose with the aid of D-xylose isomerase (DXI) inert to D-allulose to obtain an intended product having a new composition of D-glucose, D-fructose, and D-allulose.

<3> Sugar is an inexpensive sweetener in which D-glucose is bound to D-fructose and it is easily degraded with the aid of invertase. It therefore becomes an inexpensive raw material also usable for bioethanol production (refer to FIG. 5).

Sugar is not used directly as a raw material but a composition having D-glucose and D-fructose as main ingredients and obtained by (obtained by a typical production method of an invert sugar) acting invertase on the sugar and degrade it is used as the raw material. An intended product composed of rare sugar D-allulose, D-glucose and D-fructose can be obtained by acting D-allulose 3-epimerase (DAE) on the aforesaid composition to allow isomerization to proceed by an equilibrium reaction between D-fructose and rare sugar D-allulose, which reaction is for isomerizing D-fructose in the raw material into rare sugar D-allulose, and terminating the reaction at the stage when a rare sugar D-allulose content reaches an intended content of the intended product.

To summarize so far, it is preferable to use, as a raw material, an isomerized sugar or invert sugar which is a saccharide mixture having D-glucose and D-fructose as main ingredients.

[Details of Isomerized Sugar for Use as a Raw Material]

An isomerized sugar is a saccharide composed mainly of D-fructose and D-glucose and obtained by isomerizing a corn syrup composed mainly of D-glucose with an aid of an enzyme or by alkalization. In English, it is notated as "high-fructose corn syrup" and abbreviated as "HFCS". In raw material names of Japanese food, "fructose glucose syrup" can be found frequently and the notation of isomerized sugar products includes a glucose fructose syrup=a syrup having a fructose content (ratio of fructose in saccharides) of less than 50%, a fructose glucose syrup=a syrup having a fructose content of 50% or more to less than 90%, and a high fructose syrup=a syrup having a fructose content of 90% or more. In addition, there is a sugar-mixed isomerized syrup=a syrup obtained by adding 10% or more sugar to the aforesaid syrup and, if the syrup is a glucose fructose syrup, it is notated as "sugar-mixed glucose fructose syrup".

As shown in FIG. 3, an isomerized sugar is produced by a method already established. For obtaining an isomerized sugar from starch, three enzyme reactions, purification, and concentration are necessary as described below.

(1) Liquefaction: Water and α-amylase which is a hydrolase are added to starch and the resulting mixture is heated to about 95° C. By this reaction, high-molecular starch is degraded into smaller units to some extent.

(2) Saccharification: After completion of the liquefaction, the resulting liquid is cooled to about 55° C., followed by the addition of glucoamylase. By this reaction, the saccharide is degraded into smaller units and glucose is obtained.

(3) Isomerization: Glucose isomerase, an isomerization enzyme, is added at 60° C. to convert about half of the glucose into fructose. The term "isomerized sugar" is derived from this reaction (reaction of isomerizing glucose into fructose).

(4) Purification•concentration: A glucose fructose syrup having a fructose content of 42% is obtained by, after isomerization, purifying the syrup by a filtering machine or an ion exchange apparatus and evaporating water for concentration. By conducting chromatography further to increase a fructose purity, a high fructose syrup having a fructose content of 90 to 95% can be obtained. The resulting syrup is blended with a glucose fructose syrup having a fructose content of 42% to obtain a fructose glucose syrup having a fructose content of 55%.

When a high fructose syrup having a fructose content of 90 to 95% is used as a raw material, it is sometimes necessary to add, after acting the D-allulose 3-epimerase on the raw material to allow isomerization of D-fructose therein by an isomerization reaction between D-fructose and rare sugar D-allulose, and terminating the reaction at the stage when a rare sugar D-allulose content reaches an intended content of the intended product, a reaction step of acting D-xylose isomerase inert to rare sugar D-psicose on the reaction product to allow isomerization to proceed by an equilibrium reaction between D-fructose and D-glucose. Addition of the aforesaid reaction step is sometimes necessary because the intended D-fructose content of the intended product solves the problem of obesity caused by continuous intake of D-fructose and imparts the intended product with a taste quality close to that of sugar in cooperation with D-allulose and D-glucose.

[Details of Invert Sugar for Use as a Raw Material]

An invert sugar is a sweetener obtained by hydrolyzing sugar (sucrose) into fructose and glucose with the aid of an acid or an enzyme (invertase). It is sweeter than sucrose if the amount is the same so that use of an invert sugar enables a reduction in the consumption amount of sugar. In addition, having hygroscopicity, it can keep cakes moist and prevent crystallization of the sugar. Sucrose and glucose display weak right-handed optical rotation and fructose displays strong left-handed optical rotation so that an equimolecular solution of glucose and fructose displays weak left-handed optical rotation while sucrose displays weak right-handed optical rotation. Since inversion of an optical rotation plane to a polarized light occurs, it is named as "invert sugar". Sucrose does not exhibit reducibility, but the invert sugar exhibits reducibility derived from glucose.

Invertase is a yeast-derived enzyme for preparing an invert sugar by degrading (converting) sugar (sucrose) into glucose and fructose. The invert sugar is characterized by decent sweetness and mild flavor typified by honey, and has the effect of giving food a moist feel and softness and improving their color, gloss, and texture. An invert syrup is produced, for example, by keeping a 70% sucrose syrup (composed of 300 g of warm water and 700 g of sucrose) at 60° C., adding 4.2 g (corresponding to 0.6% of sucrose) of invertase to the resulting syrup, and reacting for about half a day while stirring.

[Enzyme to be Used in the Present Invention]

An enzyme D-allulose 3-epimerase (DAE) to be used in the present invention and also D-xylose isomerase (DXI) to be used at need will next be described.

The epimerase is an enzyme that when it is used for a monosaccharide, shifts the position of —OH bound to C to an opposite side and catalyzes "a reaction not causing a change in the chemical formula: $C_6H_{12}O_6$". The epimerase is therefore an enzyme belonging to the isomerase. The isomerase catalyzes "a reaction not causing a change in chemical formula". The isomerase that acts on hexose catalyzes "a reaction not causing a change in chemical formula $C_6H_{12}O_6$". For example, aldose isomerase catalyzes "transfer of hydrogen in a molecule" and promotes a redox reaction between $C_1$ and $C_2$. The isomerase is a superordinate concept of the epimerase. More specifically, the enzyme "isomerase" is well known in this industry and examples of it include ketose 3-epimerase (D-allulose 3-epimerase), D-xylose isomerase, and glucose isomerase. Glucose isomerase is however not a scientific official name. Glucose isomerase as the name of an enzyme is not included in EC number registered in International Union of Biochemistry and Molecular Biology. It is not a "scientific enzyme name". "D-xylose isomerase" is a scientific name and "glucose isomerase" is used only generally as a commercial name, because "only human beings make use of" D-xylose isomerase acting on D-glucose having a structure similar thereto and in the natural world, D-glucose is not used after conversion into D-fructose.

The epimerase is embraced in the isomerase. It is therefore possible to express it as (a) "an enzyme that isomerizes D-glucose into D-fructose" and (b) "an enzyme that isomerizes D-fructose into D-allulose".

If, for example, L-rhamnose isomerase of a certain microorganism acts on D-glucose and converts it into D-fructose, the aforesaid (a) "an enzyme that isomerizes D-glucose into D-fructose" also embraces this L-rhamnose isomerase. It also embraces all the proteins of any organisms such as microorganisms, plants, and animals that convert D-glucose into D-fructose.

It further embraces D-xylose isomerase to be used in a reaction step, when a high fructose syrup having a fructose content of 90 to 95% is used as a raw material, of acting D-xylose isomerase, which is inert to rare sugar D-psicose and is adopted at need to adjust a D-fructose content to an intended content of the intended product, on D-fructose to allow isomerization to proceed by an equilibrium reaction between D-fructose and D-glucose.

The aforesaid (b) "an enzyme that isomerizes D-fructose into D-allulose" embraces all the proteins that are produced by organisms and convert D-fructose into D-allulose.

It therefore embraces all the enzymes belonging to the EC number "EC.5.- (isomerization enzymes)". This means that it embraces a newly found enzyme or an enzyme classified into another isomerization enzyme when it has an effect of catalyzing these reactions if any. Using "isomerase" in the present invention means using a broad enzyme group.

(D-Allulose 3-Epimerase)

This enzyme is used for terminating the reaction at the stage when isomerization is allowed to proceed by an equilibrium reaction between D-fructose and rare sugar D-allulose for isomerizing D-fructose in the raw material into rare sugar D-allulose, and a content of rare sugar D-allulose reaches an intended content of an intended product. The origin or classification name of this ketohexose 3-epimerase (D-allulose 3-epimerase) is not limited insofar as it is an enzyme that isomerizes D-fructose into D-allulose.

Specific examples include bacteria (Patent Document 5) belonging to the genus *Pseudomonas* and D-ketohexose 3-epimerase (Patent Document 6 and Non-patent Document 2) derived from the *Arthrobacter globiformis* M30 strain (international deposit number NITE BP-1111). With respect to the M30 strain, transfer from NITE P-1111, which was originally deposited on Jun. 22, 2011 in the National Institute of Technology and Evaluation, Patent Microorganisms Depositary Center (2-5-8, Higashi Kazusa Kamatari, Kisarazu, Chiba, Japan), to the deposit under the Budapest treaty was requested on May 2, 2012 and it was internationally deposited under the accession number NITE BP-1111.

Ketose 3-epimerase derived from the *Arthrobacter histidinolovorans* Y586-1 strain (international deposition number: NITE BP-02813) can be given as a preferable example (International Application Indication: PCT/JP2019/045672).

The Y586-1 strain was internationally deposited on Nov. 7, 2018 in the National Institute of Technology and Evaluation, Patent Microorganisms Depositary Center at 2-5-8, Kazusa Kamatari, Kisarazu, Chiba, Japan and deposited under the accession number NITE BP-02813. The Y586-1 strain was at first identified as *Arthrobacter protophormiae*. Then, according to the identification by Japan Food Research Laboratories, it was judged as *Arthrobacter histidinolovorans* so that sequence retrieval of all the genome of the Y586-1 strain was performed. As a result, it was determined to be *Arthrobacter histidinolovorans*. The renaming of the strain having the accession number NITE BP-02813 was notified to the National Institute of Technology and Evaluation, Patent Microorganisms Depositary Center and it was approved on Oct. 4, 2019.

In ketose 3-epimerase derived from the Y586-1 strain, an enzyme produced per culture medium has an activity about twice as high as ketose 3-epimerase derived from *Arthrobacter globiformis* described in Patent Document 6 so that use of it enables efficient mass production of D-allulose. In addition, it has an enzyme optimum temperature as high as 70° C. and even at 80° C., it has relative activity of 59.4, which is about 60% assuming that the activity at the optimum temperature of 70° C. is 100. Thus, it has high heat resistance. Further, it has residual activity of 49.4% after kept at 60° C. for one hour and thus has heat tolerance so that a larger amount of a product can be obtained at a reaction at the optimum temperature of 70° C. This enzyme thus has excellent heat resistance and an amino acid-substituted variant formed therefrom can have more enhanced heat resistance.

Described specifically, by introducing mutation into a ketose 3-epimerase gene derived from the Y586-1 strain and substituting a corresponding amino acid residue by another amino acid residue by site-specific mutation operation to prepare various amino acid-substituted mutants, enzymes having higher heat resistance than wild type enzymes not substituted by an amino acid can be obtained. The mutants thus obtained can be used. They are mutants having heat resistance, whose heat resistance was evaluated by two indicators, that is, a ketose 3-epimerase activity ratio (T70/T50) at reaction temperatures of 70° C. and 50° C. and residual activity after kept at 60° C. for one hour. This makes it possible to realize an industrially-practicable and low-cost production method based on total productivity derived from high heat resistance of D-allulose 3-epimerase used and high durability (long life span) of the enzyme as a result thereof.

In Examples of the present invention, various ketose 3-epimerase mutants were prepared by causing a change by base substitution using the site-specific mutation operation and among them, those having a site from which an amino acid-substituted mutant having heat resistance higher than that of a wild type are selected in consideration of the common general technical knowledge of an enzyme that heat resistance is an important property for enhancing the life span of an enzyme. Of 37 mutated enzymes, 20 enzymes exceeded the parent-strain wild type recombinant enzyme Y586-1 strain DAE (1.78) and a test was made using the eighth amino acid-substituted mutant listed in Table 10 in the specification of the aforesaid international application.

The mutant is a protein having (1) the following mutation sequence name and (2) an amino acid sequence of SEQ ID NO: 1:

```
(1) Y586DAE_V129IA200VS218N

(2) Amino acid sequence represented by
SEQ ID NO: 1:
MKIGCHGLVWTGRFDAEGIRYSVQKTKEAGFDLIEFPLMDPFSFDVATAK

SALAEHGLTASASLGLSEATDVSSEDPAIVKAGEELLNRALDVLAELGAT

DFCGVIYSAMKKYMEPATEQGLSNSKAAIGRVVDRAAGLGINVSLEVVNR

YETNVLNTGRQALSYLSDVKRPNLGVHLDTYHMNIEESDMFSPVLDTAEV

LKYVHIGESHRGYLGTGNVDFDNFFKALGRIGYDGPVVFESFSSAVVAPD

LSRMLGIWRNLWADNEELGAHANAFIRDKLTAIKTIELH
```

By using a mutant having such heat resistance, high heat resistance and high productivity contribute to the total productivity derived from not activity but high durability (long life span) of the enzyme.

(D-Xylose Isomerase)

No limitation is imposed on the origin or name of D-xylose isomerase insofar as it has ability of isomerizing D-glucose into D-fructose (for example, Patent Documents 5 and 7). An inexpensive composition composed mainly of D-glucose and D-fructose used as a raw material can be produced by using D-glucose produced from starch and acting D-xylose isomerase on it to proceed isomerization by an equilibrium reaction between D-glucose and D-fructose.

It is also possible to use a high fructose syrup having a fructose content of 90 to 95% as a raw material in a reaction step of acting D-xylose isomerase, which is used if necessary to adjust a content of D-fructose to an intended content of an intended product and is inert to rare sugar D-psicose, on D-fructose and allowing isomerization to proceed by an equilibrium reaction between D-fructose and D-glucose (refer to FIG. 3). As D-xylose isomerase, a commercially available one can be used.

These enzymes may be purified ones or may be microorganisms producing such enzymes. In the present invention, the purified enzyme or the enzyme-producing microorganism is used as an enzyme or microorganism having the purified enzyme or the enzyme-producing microorganism immobilized thereon.

[Immobilization of Enzyme]

Using an immobilized enzyme enables a continuous massive epimerization reaction and using, as the enzyme, a heat-resistant one contributes to the prolongation of the life span.

Enzymes are most practically used when immobilized on an appropriate base material such as an ion exchange resin. As the ion exchange resin, for example, a basic anion exchange resin, either of a strongly basic anion exchange resin or a weakly basic anion exchange resin is usable. Examples of the strongly basic anion exchange resin include HPA25L (product of Mitsubishi Chemical) and IRA904CL (product of Organo). Examples of the weakly basic anion exchange resin include WA30 (product of Mitsubishi Chemical), and FPA54 and FPA95 (each, product of Organo). In Examples, a weakly basic anion exchange resin A111S of Purolite is used.

When an immobilized enzyme is prepared using the weakly basic anion exchange resin as a carrier, ketose 3-epimerase immobilized thereon can easily be eluted after it loses its isomerization capacity. The immobilization carrier can therefore be regenerated very conveniently and this leads to a reduction in production cost. Using a heat-resistant enzyme prolongs its life span and can reduce a production cost further.

For the entire production steps, either a batch system or a continuous system may be applied. In the continuous system, a raw material preparation isomerization step for acting D-xylose isomerase (glucose isomerase) on D-glucose produced from starch to prepare a mixture of D-fructose and D-glucose and an isomerization reaction step using D-allulose 3-epimerase for isomerizing D-fructose in the raw material are performed as a series of steps. Further, glucose isomerase and D-allulose 3-epimerase are used as immobilized enzymes. There has never been such a production method in which the epimerization reaction step and raw material preparation isomerization step are performed as a series of steps with the mixture of D-fructose and D-glucose as a raw material and further, the enzymes are used after respectively immobilized. This method is therefore said to be a novel production method.

For isomerization with an enzyme, the enzyme can be used in immobilized form and stable and easily usable immobilized enzymes can be obtained by various immobilization methods. Using an immobilized enzyme enables continuous and massive isomerization and isomerization reaction. For example, they are each carried out using an immobilized enzyme having an activity of 1000 U/wet weight resin (g). An immobilized enzyme can be obtained by collecting a crude enzyme solution from a solution of disrupted cells obtained, for example, by disrupting fungus body cells, passing the crude enzyme solution through an ion exchange resin packed in a column at a low temperature (4° C.) to bind a crude enzyme protein to the ion exchange resin, and passing purified water through it for washing. An immobilized system capable of withstanding continuous production can be obtained from the standpoint of stability (maintenance of activity) completely satisfactory for commercial production. A continuous and massive isomerization reaction (epimerization reaction) can be performed with the immobilized enzyme thus obtained. As the carrier for immobilizing an enzyme thereon, any known one as an immobilization carrier can be used and it is not limited to the resin carriers exemplified above.

The outline of the production method of the present invention is as shown in FIGS. 1 to 3, in which an inexpensive composition containing D-glucose and D-fructose is used as a raw material; a reaction for converting D-fructose contained in the raw material into D-allulose proceeds by passing the raw material through a bioreactor (immobilized epimerase (DAE) column); and an intended product having a new composition of D-glucose, D-fructose, and D-allulose can be obtained.

The reaction of the immobilized epimerase (DAE) column proceeds as follows: D-allulose 3-epimerase (DAE) is acted on a raw material to allow isomerization of D-fructose therein into rare sugar D-allulose to proceed by an equilibrium reaction between D-fructose and rare sugar D-allulose; the reaction is terminated at the stage when a rare sugar D-allulose content reaches that of an improved isomerized sugar or invert sugar obtained as an intended product; and then, a conversion type isomerized sugar or invert sugar composed of rare sugar D-allulose, D-glucose and D-fructose, having functionality of D-allulose, and having a taste quality close to that of sugar comes out from the column, in which the D-fructose content compensates for the disadvantage of D-allulose in sweetness degree and is in the range that makes the taste quality of the composition close to that of sugar.

[Intended Product]

The rare sugar-containing composition thus obtained is a rare sugar-containing composition (sweetener) having a taste quality equal to that of sugar, which contains D-glucose and D-fructose as an energy source at a content in the optimum range; contains sweet and delicious D-fructose in an amount adjusted so that it does not exhibit its defect (an adverse effect such as accumulation of a neutral fat by long-term continuous intake) but in an amount sufficient to compensate for the weak point of D-allulose and D-glucose in sweetness degree; and contains D-allulose in an amount that it exhibits the functionality of D-allulose.

It is sometimes necessary to control the D-allulose content so that the resulting sweetener has minimum functionality. Sport drinks and the like are better when having larger D-glucose and D-fructose contents as an energy source. In this case, the functionality of D-allulose is to suppress rapid absorption of a saccharide and maintain continuous absorption and such a function has already been found to appear at a content of 5 mass % or more. In order to administer D-allulose to people with obesity or high blood sugar levels for the purpose of treatment or prevention, a higher content is better and continuous use of it is required. The amount of D-allulose is therefore in a wide range and is 5 to 30 mass %, preferably 10 to 20 mass %.

D-allulose 3-epimerase is acted on D-fructose in the raw material to convert it into rare sugar D-allulose and thereby obtain a mixture of D-fructose and rare sugar D-allulose. The mixture of D-fructose and rare sugar D-allulose is an equilibrium mixture of D-fructose and rare sugar D-allulose or a mixture of D-fructose and rare sugar D-allulose adjusted to have an intended concentration. The content of D-allulose in the intended product can be changed by not continuing the reaction until it reaches equilibrium.

D-xylose isomerase is acted on D-glucose in the raw material to convert it into D-fructose and thereby obtain a mixture of D-glucose and D-fructose. The mixture of D-glucose and D-fructose is an equilibrium mixture of D-fructose and D-glucose or a mixture of D-glucose and D-fructose adjusted to have an intended concentration. The content of D-glucose in the intended product can be changed by not continuing the reaction until it reaches equilibrium. One of the characteristics of the sweetener containing D-glucose, D-fructose, and D-allulose, which is an intended product, is a sugar-like taste quality. D-glucose is an important ingredient as an energy and its content is preferably larger for “zero hunger”. The sweetness degree of it is 65 to 80, assuming that the sweetness of sugar is 100. The sweetness of D-fructose is necessary for a sugar-like taste quality so that the D-glucose content is determined by the D-fructose and D-allulose contents.

The sweetness degree of D-fructose is 120 to 170 and it is an important ingredient for giving sweetness to an intended product and is an ingredient giving a sugar-like taste quality to it in cooperation with D-glucose. It has however a problem as a saccharide because it causes obesity by long-term continuous intake. The D-fructose content is therefore determined by the D-glucose and D-allulose contents to obtain an intended product having a sugar-like taste quality. The D-fructose content is adjusted so as to prevent occurrence of an adverse effect of D-fructose such as accumulation of a neutral fat, compensate for the weak point of D-allulose in sweetness degree, and bring out the advantage of D-fructose that it is sweet.

Whether or not the intended product is a sweetener having a taste quality equal to that of sugar can be evaluated by expressing the sweetness degree as a calculated value based on the past results. In the present invention, therefore, the term “sugar-like taste quality”, “taste quality close to that of sugar”, “taste quality equal to that of sugar”, or the like is used when the taste quality is expressed as a calculated value close to 100 or corresponding to 100 assuming that the sweetness degree (sweetness intensity) of sugar is 100, and is used preferably when supported by an organoleptic test.

[Characteristics and Advantages of Production Method]

[Characteristic 1] An inexpensive raw material containing D-glucose and D-fructose can be used. A composition composed mainly of D-glucose and D-fructose obtained by acting D-xylose isomerase (DXI) on D-glucose produced from starch or by acting invertase on sugar to degrade it can be used.

[Characteristic 2] Since the reactions of isomerase (DXI) and epimerase (DAE) are performed separately using individual immobilization reaction columns, intended reactions can be allowed to proceed easily under appropriate conditions.

[Characteristics 3] The reactions of the two enzymes can be allowed to proceed under appropriate conditions, respectively so that it is possible to respond to a reduction in activity or the like by replacing only the defective one.

[Characteristics 4] Two enzyme reactions are performed separately, making it possible to make the reaction of only an intended saccharide. The main characteristic is that by controlling the two reactions skillfully according to the specificity of them, the intended product thus obtained is a rare sugar-containing composition (sweetener) containing glucose as an energy source at a content in the optimum range; containing sweet and delicious D-fructose in an amount adjusted so that it does not exhibit its defect (an adverse effect such as accumulation of a neutral fat by long-term continuous intake) but in a sufficient amount to compensate for the weak point of D-allulose in sweetness degree; containing such an amount of D-allulose as to have the functionality of D-allulose; and thereby having a taste quality equal to that of sugar.

[Advantage 1] A product in pure form and not containing a by-product can be produced by using various isomerized sugars for which a mass production technology has been established (which can be produced only by an epimerase column and useful for the production of a product having an expected composition by properly using the various ones) and inexpensive sugar (sugar mass produced and used for bioethanol and having a D-glucose+D-fructose (1:1) composition can be used at a low cost) and connecting a conventional production line in a proper form.

[Advantage 2] An epimerase (DAE) column necessary for producing the present rare sugar-containing composition may be connected as is to an isomerase (DXI) column which is generally used for the production of an isomerized sugar or invert sugar. This therefore enables production at a very low cost.

[Advantage 3] The present rare sugar-containing composition can have a constant composition or a varied composition easily by adjusting the enzyme reaction of isomerase (DXI) in the raw material production stage and that of epimerase (DAE) in the D-allulose production stage.

[Advantage 4] The production step does not include a separation procedure so that the production step can be carried out simply. This not only reduces the cost considerably and but also facilitates management of the production step.

[Advantage 5] In the production step, the raw material or the product is not lost by a separation operation or the like during production and 100% of the raw materials can be obtained theoretically as a product.

[Advantage 6] Products different in composition ratio can also be obtained by adjusting two enzyme activities or a passing rate through a reaction column. An intended product having an intended composition can be obtained by adjusting at least one selected from the group consisting of, as well as a flow rate of the substrate, a reaction time with the substrate, a reaction temperature, pH of a substrate solution, and an amount of the enzyme.

[Advantage 7] An industrially-practicable and low-cost production method can be provided based on the total productivity derived from the high heat resistance of D-allulose 3-epimerase used and the high durability (long life span) of the enzyme as a result thereof.

The novel sweetener thus obtained can be used in combination with a sweetener such as sucrose, sugar alcohol, aspartame, or stevia, if desired. Water-soluble dietary fibers having a low sweetness degree (such as polydextrose, inulin, or indigestible dextrin) may be added as needed to impart the composition with body feeling.

The sweetener of the present invention embraces an aspect of a rare sugar-containing composition having D-glucose, D-fructose, and D-allulose at 58:29.4:12.6 or 45:38.5:16.5, but when the composition is used while making use of its sweetness degree and sweetness quality, its content is not particularly limited. The content can be adjusted as needed, depending on the degree of intended function, using aspect, using amount, or the like.

The novel sweetener of the present invention having a taste quality equal to that of sugar contains D-allulose and has an obesity preventing effect. It can also be used in combination with another active ingredient for preventing lifestyle-related diseases.

[Uses]

The sweetener composition of the present invention composed of rare sugar D-allulose, D-glucose, and D-fructose and having a taste quality equal to that of sugar is used similarly for known uses of a rare sugar-containing composition composed of D-glucose, D-fructose, and D-allulose.

The sweetener composition of the present invention is characterized by that it is a product of raw material isomerized sugar or invert sugar and is a product not subjected to a separating operation by simulated moving bed chromatography. It is also characterized by that it is a product of raw material isomerized sugar or invert sugar and a liquid syrup obtained by passing through an immobilized enzyme reaction column. It is a composition of D-glucose, D-fructose, and D-allulose so that it is also used for the uses described in Patent Document 7. Glucose, fructose, and D-allulose each belong to food (certified as food) so that they are very safe and easy to handle as a food mixture. D-allulose (=D-psicose) is present in trace amounts in food materials and is highly safe. Due to the development of a mass production technology of it, it has recently a high utility value also in cost. It has already been known to show 5,000 mg/kg or more in an acute oral toxicity test.

Examples of the uses of a saccharide composition containing D-allulose (D-psicose) include food, beverages, particularly functional food (for obesity prevention), pharmaceuticals, cosmetics, feed, agricultural chemicals (plant growth regulators, plant disease resistance amplifiers, and the like) and industrial use. Sweeteners having a taste quality equal to that of sugar can be used for anything requiring a sweet taste such as food, health food, food for patients, food materials, health food materials, food materials for patients, food additives, health food additives, food additives for patients, beverages, health beverages, beverages for patients, drinking water, health drinking water, drinking water for patients, drugs, raw materials for pharmaceutical, feed, and feed for patient livestock and/or patient animals.

When the sweetener of the present invention having a taste quality equal to that of sugar is used for food, it may be provided as is or may be prepared in a form diluted in water or the like, in a form suspended in oil or the like, as a meal in milky liquid form, or in a carrier-added form generally used in the food industry. The beverage is provided as a non-alcoholic beverage or an alcoholic beverage. Examples of the non-alcoholic beverage include carbonated beverages, non-carbonated beverages such as fruit juice beverages and nectar beverages, soft drinks, sports drinks, tea, coffee, and cocoa. Examples of the form of alcoholic beverage include beer, low-malt beer-like beverages, malt-free beer-like alcoholic beverages, sake, plum wine, wine, champagne, liqueur, white liquor highball, and medicinal alcoholic beverages.

When the rare sugar-containing composition of the present invention is used as a food material or food additive used for the purpose of improving the abnormal sugar metabolism and/or abnormal lipid metabolism, it is provided as tablets, capsules, powdery or granular solid agents to be dissolved in beverage or the like, semi-solids such as jelly, liquids such as drinking water, and highly-concentrated solutions to be diluted upon use.

Further, the sweetener of the present invention having a taste quality equal to that of sugar can be added to food as needed to obtain a health food or a food for the sick for the purpose of improving abnormal sugar metabolism and/or abnormal lipid metabolism. As an optional ingredient, vitamins, carbohydrates, coloring matters, flavoring agents, and the like that are usually added to food may be blended as needed. The food can be taken in any liquid or solid form. It can be taken in the form of a soft capsule obtained by encapsulating with gelatin or the like. The capsule is made of a gelatin film prepared by adding water to raw material gelatin to dissolve it and adding a plasticizer (glycerin, D-sorbitol, etc.) to the resulting solution. The sweetener of the present invention having a taste quality equal to that of sugar can be used as a sweetener for the same uses of sugar. It can also be used for cooking, tea, coffee, seasonings (such as mirin), or the like.

The following are specific examples of food and beverages. Examples include western-type confectionary (pudding, jelly, gummy candy, candy, drop, caramel, chewing gum, chocolate, pastry, butter cream, custard cream, cream puff, pancake, bread, potato chip, fried potato, popcorn, cracker, pie, sponge cake, castella, waffle, cake, doughnut, biscuit, cookie, rice cracker, “okaki” cracker, “okoshi”, sweet bun, candy etc.), dried noodle products (macaroni, pasta), egg products (mayonnaise, fresh cream), beverages (functional beverage, fermented lactic beverage, lactic acid bacteria beverage, concentrated dairy beverage, fruit juice beverage, fruit juice-free beverage, fruit pulp beverage, clear carbonated beverage, carbonated beverage with fruit juice, colored carbonated beverage with fruit), luxury products (green tea, black tea, instant coffee, cocoa, canned coffee drink), dairy products (ice cream, yogurt, coffee milk, butter, butter sauce, cheese, fermented milk, processed milk), pastes (marmalade, jam, flower paste, peanut paste, fruit paste, fruit preserved in syrup), livestock meat products (ham, sausage, bacon, dry sausage, beef jerky, lard), seafood products (fish ham, fish sausage, boiled fish-paste, tube-shaped fish paste cake, cake of ground fish combined with starch and steamed, dried fish, dried-bonito, dried-mackerel, dried boiled fish, sea urchin egg, fermented squid product, dried squid, fish dried with mirin, dried shellfish, smoked products such as smoked salmon), preserved food boiled in soy (small fish, shellfish, wild vegetable, mushrooms, kelp), curry (instant curry, retort-pouch curry, canned curry), seasonings (miso, powdered miso, soy sauce, powdered soy sauce, unrefined sake, fish sauce, sauce, ketchup, oyster sauce, solid bouillon, sauce for grilled meat, curry roux, stew mix, soup mix, instant bouillon, paste, instant soup, seasoned powder for sprinkling, dressing, salad oil), fried products (deep fried bean curd, fried confectionery, instant Chinese noodles), soy milk, margarine, and shortening.

The above-described food and beverages can be produced by blending the composition with raw materials of general food and processing by the conventional method. Although the blending amount of the composition in the food and beverages varies depending on the form of the food and is not particularly limited, it is usually preferably from 0.1 to 50 wt %.

The above-described food and beverages can also be used as functional food, nutritional supplementary food, or health food. The form of them is not particularly limited and production examples of food include highly nutritional milk proteins with good amino acid balance such as milk protein, soy protein, and egg albumin, degradation products thereof, oligopeptide of albumen, and soybean hydrolysate and also mixtures of simple amino acids. They can be used by the conventional method. They can also be used in the form of a soft capsule, a tablet, or the like.

Examples of the nutritional supplementary food or functional food include processed forms such as liquid food, semi-digested nutritional food, ingredient nutritional food, health drinks, capsules, and enteral nutrients, each containing saccharides, fats, trace elements, vitamins, emulsifiers, and flavoring agents. The above-described various foods, for example, food and beverages such as sports drinks and nutritional drinks may be supplemented further with nutritional additives such as amino acids, vitamins and minerals, sweeteners, spices, flavoring agents, and coloring matters to improve their nutritional balance and flavor.

The functional food is suited for use in the field of health food or preventive medicines for preventing a specific disease (obesity prevention). The health food for preventing a specific disease may contain as needed, in addition to a saccharide composition containing rare sugar D-allulose (D-psicose) as an essential ingredient, an optional ingredient such as vitamins, carbohydrates, coloring matters, flavoring agents, and the like which have been added usually to food. The food can be taken in any liquid or solid form. It can be taken in the form of a soft capsule obtained by encapsulating with gelatin or the like. The capsule is made of a gelatin film prepared by adding water to raw material gelatin to dissolve it and adding a plasticizer (glycerin, D-sorbitol, etc.) to the resulting solution.

When the sweetener of the present invention having a taste quality equal to that of sugar is used as a food additive, its form can be selected as needed. Examples include food prepared with the sweetener of the present invention containing rare sugar D-allulose (=D-psicose) as is, food prepared with the sweetener as an additive, and optional forms, such as capsules and tablets, conventionally used for food or health food. When the sweetener is taken or administered after blended in food, it may be mixed with an excipient, extender, binder, thickener, emulsifier, coloring material, flavoring agent, food additive, seasoning, or the like as needed and the resulting mixture may be formed into powders, granules, tablets, or the like, depending on the intended use. Further, the sweetener can be taken after it is mixed in a food material to prepare a food and the food thus obtained is then industrialized as a functional food.

The sweetener composition of the present invention can be applied to feed for livestock, poultry and pets. For example, it can be blended in dry dog food, dry cat food, wet dog food, wet cat food, semi-moist dog food, poultry feed, and feed for livestock such as cattle and pigs. The feed itself can be prepared by the conventional method.

These therapeutic agents and preventives can also be used for non-human animals, for example, domestic mammals such as cattle, horses, pigs, and sheep, poultry such as chickens, quails, and ostriches, pets such as reptiles, birds, and small mammals, and farmed fish.

Drugs intended to express physiological action and thereby achieve an effect of improving saccharide metabolism abnormalities and/or lipid metabolism abnormalities or an effect of improving obesity, while making use of the sweetness of the sweetener of the present invention may be not only used alone but also blended with an appropriate additive such as general excipient, stabilizer, preservative, binder, or disintegrant, formulated into an appropriate dosage form selected from liquids, granules, fine granules, powders, tablets, capsules, pills, sprays, or spraying agents, and then, orally or nasally administered.

For preparing the composition of the present invention as a drug, usable are pharmaceutical organic or inorganic solids, semi-solid or liquid carriers, and solubilizers or diluents suited for oral or nasal administration. Any of water, gelatin, lactose, starch, magnesium stearate, talc, animal or vegetable oil, benzyl alcohol, gum, polyalkylene glycol, petroleum resin, coconut oil, lanolin, and other carriers (carriers) for pharmaceuticals can be used as a carrier of a drug containing the composition of the present invention. Further, stabilizers, wetting agents, emulsifiers, and salts for changing the osmotic pressure or maintaining an appropriate pH of an agent to be blended can be used as needed as an adjuvant.

When the composition is used as a pharmaceutical composition, a known method can be used for the preparation thereof. The dosage form can be selected as needed. As such a dosage form, for example, when it is prepared as an orally administrable preparation, examples of the dosage form include tablets, granules, powders, capsules, coating agents, liquids, and suspensions. When it is prepared as a parenterally administrable administration, examples of the dosage form include injections, drops, and suppositories. The dose of the pharmaceutical composition can be set as needed, depending on its form, administration route, and using purpose and the age, weight, and symptom of a subject to be administered. In the drug, a saccharide composition containing rare sugar D-allulose (D-psicose) as an active ingredient can be used not only as is but also as a pharmaceutically acceptable salt thereof. As the drug, the sweetener composition containing D-allulose (=D-psicose) may be used singly as a preparation or it may be used after processing into a preparation composition by adding a pharmaceutically usable carrier or diluent. Such a preparation or drug composition can be administered, as described above, through an oral route or a parenteral route. For example, a solid or fluid (gel and liquid) preparation or drug composition for oral administration is provided in the form prepared as tablets, capsules, tablets, pills, powders, granules, or gels. An accurate dose of the preparation or drug composition changes with the intended use form or treatment time so that it is an adequate amount determined by a doctor or veterinarian in charge. A dose or administration amount can be adjusted as needed by the preparation form. A daily dose of an oral solid preparation such as tablets or that of an oral liquid may be administered once or in several portions. In a preparation form such as syrup, troches, or chewable tablets which infants take to cause local action and also cause systemic action by oral administration, ½ to ⅒ of a daily dose may be blended and administered as a single dose and in this case, a total dose does not necessarily satisfy a daily dose.

On the contrary, if an administration amount is reasonable judging from the preparation form, an amount corresponding to a daily dose may be blended for a single dose. In obtaining a preparation, ordinarily usable fillers, extenders, binders, disintegrants, surfactants, lubricants, coating agents, sustained release agents, diluents, and excipients can be used. In addition, usable are solubilizing agents, buffers, preservatives, solubilizers, isotonizing agents, emulsifying agents, suspending agents, dispersants, thickeners, gelling agents, curing agents, absorbents, adhesives, elasticity imparting agents, plasticizers, adsorbents, flavoring agents, coloring agents, taste corrigents, antioxidants, moisturizing agents, light shielding agents, brighteners, antistatic agents, and the like.

The present invention can provide a skin external preparation making use of the skin moisturizing, skin antioxidant, and skin antiaging effects of rare sugar D-allulose (D-psicose), that is, a skin external preparation which has skin roughness or dryness improving and preventive effects and is known as a remedy, a skin external preparation, a cosmetic, or the like (Patent Document 8). The skin external preparation according to the present invention may contain, in addition to a saccharide composition containing rare sugar D-allulose (D-psicose) as an essential ingredient, ingredients ordinarily used for skin external preparations such as cosmetics and pharmaceuticals, for example, water-based ingredients, oily ingredients, powdery ingredients, alcohols, moisturizing agents, thickeners, ultraviolet absorbers, whitening agents, antiseptics, antioxidants, surfactants, perfumes, coloring agents, and various skin nutrition agents as needed, if necessary. Further, skin external preparations may contain metal sequestering agents such as disodium edetate, trisodium edetate, sodium citrate, sodium polyphosphate, sodium metaphosphate, and gluconic acid, hot water extracts such as caffeine, tannin, verapamil, herbal extracts, glabridin, and Chinese quince, various crude drugs, drugs such as tocopherol acetate, glycyrrhizic acid, and tranexamic acid and derivatives thereof, or salts thereof, Vitamin C, magnesium ascorbate phosphate, glucoside ascorbate, arbutin, kojic acid, and saccharides such as D-glucose, D-fructose, and trehalose. This means that a skin external preparation can be produced by blending, in a saccharide composition containing rare sugar D-allulose (D-psicose), a raw material ordinarily used for skin external preparation, for example, an oil or fat such as vegetable oil, a wax such as lanolin or beeswax, a hydrocarbon, a fatty acid, a higher alcohol, an ester, a surfactant, a coloring matter, a perfume, a vitamin, an extracted ingredient from vegetable or animal, ultraviolet absorber, antioxidant, antiseptic, or bactericide. An herbal extract ingredient such as glycyrrhetinic acid, diphenhydramine hydrochloride, azulene, dl-α-tocopherol and derivatives thereof, vitamin B2, vitamin B6, and the like which are raw materials for anti-inflammatory skin external preparations may be used in combination. The skin external preparation may be provided in any form such as ointment, cream, milky lotion, lotion, pack, or bath additive insofar as it is conventionally used for skin external preparations and the dosage form is not particularly limited. When the composition is used for a skin external preparation, the dosage form can be selected as needed. Examples include a solution system, a solubilized system, an emulsified system, a powder dispersion system, a water-oil two-layer system, a water-oil-powder three-layer system, gel, mist, spray, mousse, roll-on, and stick and further, a preparation obtained by impregnating a sheet such as nonwoven cloth with the composition or applying the composition thereto.

With a view to providing a material having possibility of remarkably reducing the using amount of an agricultural chemical and having amplifying action of plant disease resistance, another group of the present inventors have already registered an invention of a plant disease resistance amplifying agent containing a rare sugar (Patent Document 9). Since then, the research and development of it have proceeded rapidly and there is a plurality of patents on it.

The composition can be used as a sweetener to be added to a toothpaste.

Further, a soluble film has been used for preparing cosmetics and the like. For example, an edible soluble film is used as a flavor film or the like having a flavoring agent or the like retained thereon for the purpose of mood change, prevention of bad breath, or the like. There is proposed a soluble film which exhibits excellent solubility and film properties as a packing material of food, pharmaceuticals, and the like or as a carrier for supporting thereon an active ingredient of food, pharmaceuticals, or the like and is suitably used for these applications (Patent Document 10). Thus, the sweetener of the present invention having a sweetness degree and a sweet taste equal to those of sugar can be suited to pharmaceuticals, quasi drugs, and cosmetics.

The blending amount in food, beverage, cosmetic, or feed is not particularly limited, but about 0.01 to 10 wt % of D-allulose (=D-psicose) is preferred. In the case of a pharmaceutical, it can be orally administered as a capsule, powder, or tablet. Since it is soluble in water, an administration route such as intravenous injection or intramuscular injection may be used as well as oral administration. The dose differs depending on the degree of the symptom of, for example, diabetes, weight, age, sex, or the like. Upon use, an appropriate dose is desirably determined depending on the symptom. The blending amount in a pharmaceutical is not particularly limited, but about 0.01 to 2,000 mg of D-allulose (=D-psicose) is preferred for oral administration, about 0.01 to 1,000 mg for intravenous injection administration, and about 0.01 to 1,000 mg for intravenous injection administration, each per kg of weight.

The present invention will be described in further detail by Examples, but the present invention is not limited to or by Examples.

Examples

As D-allulose 3-epimerase, the protein having an amino acid sequence represented by SEQ. ID NO: 1 was used. As an immobilization carrier, a weakly basic anion exchange resin A111S of Purolite was used.

[Production of New Sweetener in the Batch Method]

An enzyme reaction was conducted by weighing 3 ml of an immobilized enzyme on which D-allulose 3-epimerase was immobilized, adding a 60% saccharide solution, and shaking the resulting mixture at 60° C. The saccharide solutions used as a substrate were a 55:45 D-glucose:D-fructose solution, a 50:50 D-glucose:D-fructose solution, and a 45:55 D-glucose:D-fructose solution, respectively.

Figure 6:
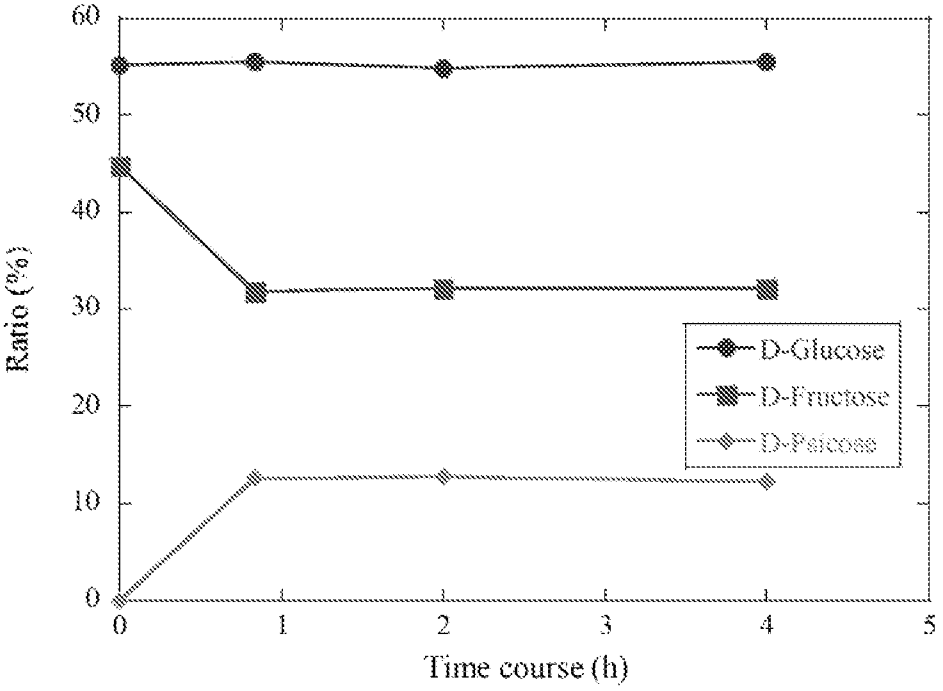
FIG. 6 is a line graph showing a time-dependent change of a saccharide solution in batch method when a syrup having a D-glucose:D-fructose ratio of 55:45 was used as a substrate of Example 1.

When the 55:45 D-glucose:D-fructose solution was used, the saccharide composition in the equilibrium condition was 55.6:32.1:12.3 D-glucose:D-fructose:D-allulose (FIG. 6).

Figure 7:
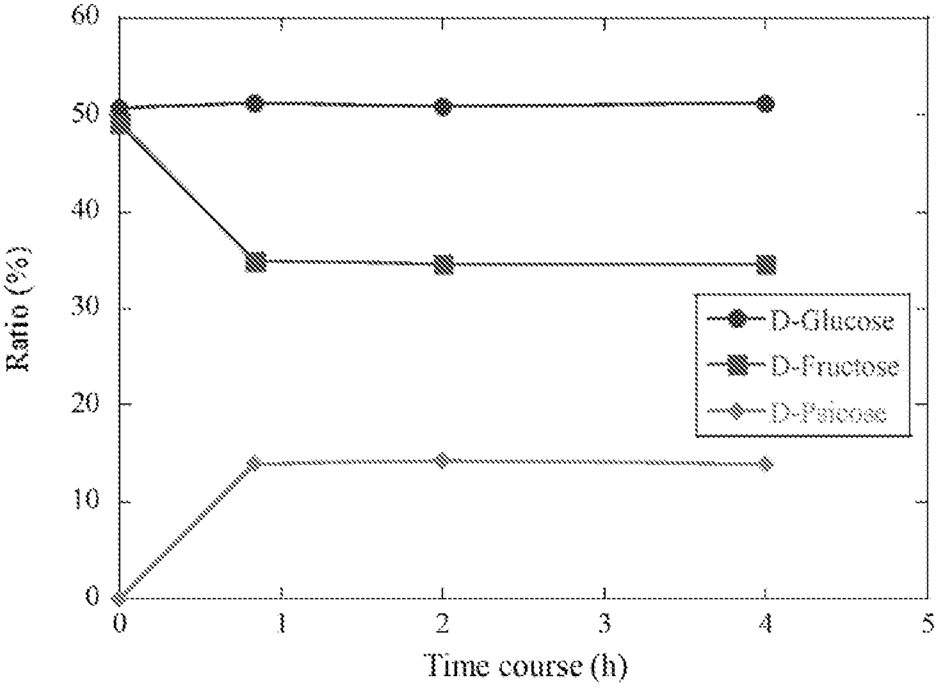
FIG. 7 is a line graph showing a time-dependent change of a saccharide solution in batch method when a syrup having a D-glucose:D-fructose ratio of 50:50 was used as a substrate of Example 1.

When the 50:50 D-glucose:D-fructose solution was used, the saccharide composition in the equilibrium condition was 51.0:34.7:14.3 D-glucose:D-fructose:D-allulose (FIG. 7).

Figure 8:
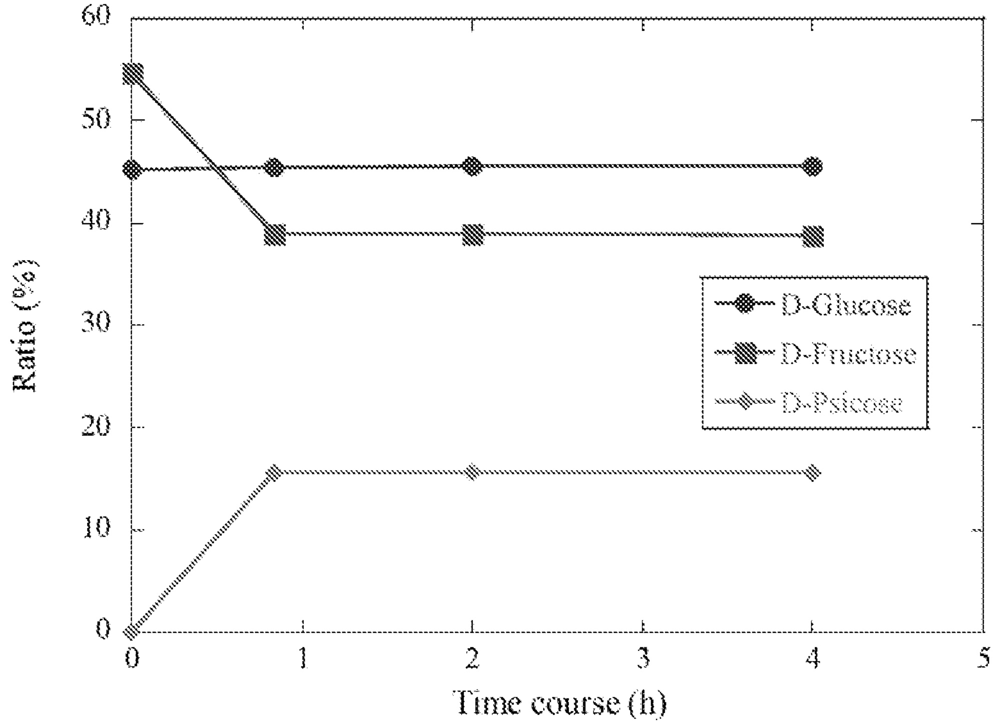
FIG. 8 is a line graph showing a time-dependent change of a saccharide solution in batch method when a syrup having a D-glucose:D-fructose ratio of 45:55 was used as a substrate of Example 1.

When the 45:55 D-glucose:D-fructose solution was used, the saccharide composition in the equilibrium condition was 45.6:38.8:15.6 D-glucose:D-fructose:D-allulose (FIG. 8).

[Production of New Sweetener by the Column Method]

A bioreactor was constructed by packing a jacket column with about 250 mL of an immobilized enzyme having D-allulose 3-epimerase immobilized thereon. An enzyme reaction was conducted by using a 60% saccharide solution as a substrate, circulating warm water of 60° C. in the jacket part, and changing the flow rate from SV=1 to SV=5. The saccharide solutions used as the substrate were 58:42 D-glucose:D-fructose, 50:50 D-glucose:D-fructose, and 45:55 D-glucose:D-fructose.

The results of changing a saccharide composition by the column method when SV was changed using a 58:42 D-glucose:D-fructose saccharide solution as a substrate are shown in Table 1.

The results of changing a saccharide composition by the column method when SV was changed using a 50:50 D-glucose:D-fructose saccharide solution as a substrate are shown in Table 2.

The results of changing a saccharide composition by the column method when SV was changed using a 42:58 D-glucose:D-fructose saccharide solution as a substrate are shown in Table 3.

TABLE 1

| | Substrate | SV = 1 | SV = 2 | SV = 3 | SV = 4 | SV = 5 |
|---|---|---|---|---|---|---|
| D-Glucose | 58.59 | 59.06 | 58.99 | 59.04 | 59.08 | 59.02 |
| D-Fructose | 41.41 | 29.18 | 29.22 | 29.43 | 29.92 | 30.35 |
| D-Psicose | 0.00 | 11.76 | 11.79 | 11.53 | 11.00 | 10.63 |

TABLE 2

| | Substrate | SV = 1 | SV = 2 | SV = 3 | SV = 4 | SV = 5 |
|---|---|---|---|---|---|---|
| D-Glucose | 50.86 | 51.29 | 51.20 | 51.13 | 51.14 | 51.15 |
| D-Fructose | 49.14 | 34.72 | 34.95 | 35.51 | 36.36 | 37.09 |
| D-Psicose | 0.00 | 14.00 | 13.85 | 13.36 | 12.50 | 11.77 |

TABLE 3

| | Substrate | SV = 1 | SV = 2 | SV = 3 | SV = 4 | SV = 5 |
|---|---|---|---|---|---|---|
| D-Glucose | 42.92 | 43.23 | 43.15 | 43.20 | 43.19 | 43.11 |
| D-Fructose | 57.08 | 40.28 | 40.74 | 42.01 | 43.29 | 44.38 |
| D-Psicose | 0.00 | 16.49 | 16.11 | 14.79 | 13.51 | 12.51 |

INDUSTRIAL APPLICABILITY

Mass production of a sweetener which does not cause lifestyle-related diseases such as obesity even if used widely in a food industry or the like and has a sweetness degree and a taste quality almost similar to those of sugar is expected to be achieved at a world scale and a low cost with sufficient cost competitiveness. Due to success in mass production at a low cost and a world scale, expected is not only the expansion of the use of a saccharide composition containing D-allulose (=D-psicose) as food and beverages, particularly functional food (for obesity prevention, or the like), pharmaceuticals, cosmetics, feed, agricultural chemicals (such as plant growth regulator and plant disease resistance amplifier), and industrial products but also the supply of it to the world as an energy source or the like for "zero hunger".

The invention claimed is:

1. A method for mass-producing a sweetener containing three saccharides D-glucose, D-fructose, and D-allulose, having functionality of D-allulose, and having a taste quality close to that of sugar, comprising:

using, as a raw material, an inexpensive composition containing D-glucose and D-fructose, acting D-allulose 3-epimerase on the raw material to allow isomerization of D-fructose therein to proceed by an isomerization reaction between D-fructose and rare sugar D-allulose, terminating the reaction at a stage when a rare sugar D-allulose content reaches an intended content of an intended product, and obtaining the intended product having, in a composition of rare sugar D-allulose, D-glucose, and D-fructose, a D-fructose content in a range that compensates for a weak point of D-allulose in a sweetness degree and gives the intended product a taste quality close to that of sugar in cooperation with D-allulose and D-glucose, wherein:

world scale mass production with sufficient price competitiveness is achieved by using, as the D-allulose 3-epimerase, D-allulose 3-epimerase having high heat resistance and high productivity and derived from *Arthrobacter histidinolovorans* to realize total productivity depending on the high heat resistance and high durability (long life span) of the enzyme as a result thereof and performing production without using simulated moving bed chromatography.

2. The method according to claim 1, wherein:

contents of individual ingredients are determined to obtain an appropriate composition suited for a purpose after consideration of the following characteristics of the ingredients:

D-glucose is important as an energy source in the intended product and has a sweetness intensity of 65 to 80 assuming that a sweetness intensity of sugar is 100;

D-fructose has a sweetness intensity of 120 to 170, is important for giving sweetness, and gives a taste quality close to that of sugar in cooperation with D-allulose and D-glucose, but has a problem as a saccharide causing obesity by continuous intake; and D-allulose has a sweetness intensity of 70 and is capable of giving such physiological functions as obesity prevention and suppression of a sudden blood sugar level rise.

3. The method according to claim 1, wherein the raw material is a composition containing D-glucose and D-fructose and produced by acting D-xylose isomerase on D-glucose produced from starch and allowing isomerization to proceed by an equilibrium reaction between D-glucose and D-fructose or produced by acting invertase on sugar to degrade the sugar.

4. The method according to claim 1, wherein the raw material is an inexpensive isomerized sugar or invert sugar and the intended product is an improved isomerized sugar or invert sugar having functionality of D-allulose, having a taste quality close to that of sugar, and exhibiting an excellent physiological effect without causing a disease by continuous intake.

5. The method according to claim 4, wherein a glucose fructose syrup and/or a fructose glucose syrup is used as the inexpensive isomerized sugar as the raw material.

6. The method according to claim 1, wherein the rare sugar D-allulose content of the intended product is attained by adjusting an enzyme activity of the D-allulose 3-epimerase used.

7. The method according to claim 1, wherein the isomerization reaction is performed by passing a substrate solution through an immobilized enzyme column and the intended product having an intended composition is obtained by adjusting one or more factors selected from the group consisting of a flow rate of the substrate, a reaction time with the substrate, a reaction temperature, pH of the substrate solution, and an amount of the enzyme.

8. The method according to claim 1, wherein a 100% intended product is obtained using an immobilized enzyme reaction with the raw material as a substrate without producing a by-product theoretically.

9. The method according to claim 1, further comprising, after acting the D-allulose 3-epimerase on the raw material to allow isomerization of D-fructose therein to proceed by an isomerization reaction between D-fructose and rare sugar D-allulose and terminating the reaction at a stage when a rare sugar D-allulose content reaches an intended content of the intended product, a reaction step for acting D-xylose isomerase inert to the rare sugar D-allulose on the reaction product to allow isomerization to proceed by an equilibrium reaction between D-fructose and D-glucose.

10. The method according to claim 9, wherein a high fructose syrup is used as the inexpensive isomerized sugar as the raw material.

11. The method according to claim 2, wherein the raw material is a composition containing D-glucose and D-fructose and produced by acting D-xylose isomerase on D-glucose produced from starch and allowing isomerization to proceed by an equilibrium reaction between D-glucose and D-fructose or produced by acting invertase on sugar to degrade the sugar.

12. The method according to claim 2, wherein the raw material is an inexpensive isomerized sugar or invert sugar and the intended product is an improved isomerized sugar or invert sugar having functionality of D-allulose, having a taste quality close to that of sugar, and exhibiting an excellent physiological effect without causing a disease by continuous intake.

13. The method according to claim 12, wherein a glucose fructose syrup and/or a fructose glucose syrup is used as the inexpensive isomerized sugar as the raw material.

14. The method according to claim 2, wherein the rare sugar D-allulose content of the intended product is attained by adjusting an enzyme activity of the D-allulose 3-epimerase used.

15. The method according to claim 2, wherein the isomerization reaction is performed by passing a substrate solution through an immobilized enzyme column and the intended product having an intended composition is obtained by adjusting one or more factors selected from the group consisting of a flow rate of the substrate, a reaction time with the substrate, a reaction temperature, pH of the substrate solution, and an amount of the enzyme.

16. The method according to claim 2, wherein a 100% intended product is obtained using an immobilized enzyme reaction with the raw material as a substrate without producing a by-product theoretically.

17. The method according to claim 2, further comprising, after acting the D-allulose 3-epimerase on the raw material to allow isomerization of D-fructose therein to proceed by an isomerization reaction between D-fructose and rare sugar D-allulose and terminating the reaction at a stage when a rare sugar D-allulose content reaches an intended content of the intended product, a reaction step for acting D-xylose isomerase inert to the rare sugar D-allulose on the reaction product to allow isomerization to proceed by an equilibrium reaction between D-fructose and D-glucose.

18. The method according to claim 17, wherein a high fructose syrup is used as the inexpensive isomerized sugar as the raw material.

* * * * *